(12) United States Patent
Assmann et al.

(10) Patent No.: US 6,387,939 B1
(45) Date of Patent: May 14, 2002

(54) HALOGENZIMIDAZOLES AND THEIR USE AS MICROBICIDES

(75) Inventors: Lutz Assmann, Eutin; Albrecht Marhold; Ralf Tiemann, both of Leverkusen; Klaus Stenzel, Düsseldorf, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/636,720

(22) Filed: Aug. 11, 2000

Related U.S. Application Data

(62) Division of application No. 09/387,719, filed on Aug. 25, 1999, now Pat. No. 6,160,001, which is a division of application No. 09/011,250, filed as application No. PCT/EP96/03334 on Jul. 29, 1996, now Pat. No. 6,020,354.

(30) Foreign Application Priority Data

| Aug. 10, 1995 | (DE) | ......................................... | 195 29 407 |
| Mar. 8, 1996 | (DE) | ......................................... | 196 09 060 |

(51) Int. Cl.⁷ ......................... A01N 43/52; C07D 409/12
(52) U.S. Cl. ..................... 514/395; 514/80; 548/302.1; 548/304.7
(58) Field of Search ................. 514/80, 395; 548/392.1, 548/304.7

(56) References Cited

U.S. PATENT DOCUMENTS 3,988,465 A    10/1976   Rochling

FOREIGN PATENT DOCUMENTS

| EP | 545204 | 6/1993 |
| GB | 1114943 | 5/1968 |
| GB | 1306098 | 2/1973 |

OTHER PUBLICATIONS

Chemical Abstracts, vol. 114, No. 15, Apr. 15, 1991, Abstract No. 143420v, M.W. Moon, et al. "Preparation o aminoheterocycloquinolines . . . agents", p. 785; Chemical Abstracts, Chemical Substances, 12th Collective Index, vol. 106–115, 1987–1991, Seite 13453CS: die Verbindugen mit den RN [132873–97–3] und [132873–96–2] & WO 90 15058 A (Upjohn Co.) 13. Dec. 1990.
Journal of Organic Chemistry, Bd, 49, Nr. 12, 15. Jun. 1984, Easton US, p. 2158–2164, XP002019110, T.M. Stevenson, et al.: "Defined Dimensional Alterations . . . lin–Naphthoadenosine", p. 2159; Spalte 1, Schema 1, die Verbindung Nr. 10.

Journal of the Chemical Society, 1963, Letchworth, GB, p. 2930–2937, XP002019111, D. Harrison, et al.: "Some 1–and 2–Halogenobenzimidazoles." p. 2936, Absatz 8.

Primary Examiner—Patricia L. Morris
(74) Attorney, Agent, or Firm—Norris McLaughlin & Marcus

(57) ABSTRACT

New halogenobenzimidazoles of the formula

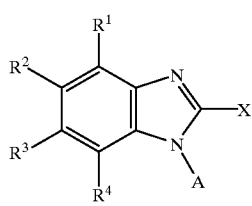

(I)

in which

A, $R^1$, $R^2$, $R^3$, $R^4$ and X have the meanings given in the description, and their acid addition salts and metal salt complexes, a process for their preparation and their use as microbicides in crop protection and in the protection of materials.

New intermediates of the formulae

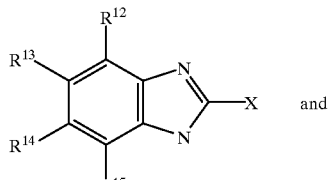 and

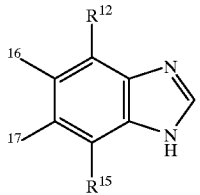

in which $R^{12}$–$R^{17}$ and X have the meanings given in the description, and processes for the preparation of these substances.

4 Claims, No Drawings

HALOGENZIMIDAZOLES AND THEIR USE AS MICROBICIDES

This application is a divisional of application Ser. No. 09/387,719, filed Aug. 25, 1999, now U.S. Pat. No. 6,160,001, issued Dec. 12, 2000, which is a divisional of application Ser. No. 09/011,250, filed Jan. 28, 1998, now U.S. Pat. No. 6,020,354, issued Feb. 1, 2000, which is, in turn, a 371 of PCT/EP96/03334, filed on Jul. 29, 1996.

The present invention relates to new halogenobenzimidazoles, to a process for their preparation, and to their use as microbicides in crop protection and in the protection of materials. The invention furthermore relates to new intermediates and to a process for their preparation It has already been disclosed that certain bemidazole derivatives have fungicidal properties (cf. DE-A 4 139 950 and EP-A 0 517 476). 2-Cyano-3-dimethylaminosulphonyl-6,6,7,7-tetrafluoro-[1,4]dioxino[2,3-f]benzimidazole and 2-cyano-6,6-difluoro-2-methylaminosulphonyl-[1,3]dioxolo[4,5-f]benzimidazole, for example, can be employed for controlling fungi. The efficacy of these substances is good, but leaves something to be desired in some cases hen low rates of application are used.

There have now been found new halogenobenzimidazoles of the formula

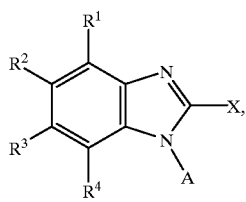

(I)

in which
R$^1$, R$^2$, R$^3$ and R$^4$ independently of one another represent hydrogen, halogen, cyano, nitro, alkyl, halogenoalkyl, alkoxy, halogenoalkoxy, alkylthio, halogenoalkylthio, alkylsulphinyl, halogenoalkylsulphinyl, alkylsulphonyl, halogenoalkylsulphonyl, optionally substituted cycloalkyl, hydroxycarbonyl, alkylcarbonyl alkoxycarbonyl; cycloalkylcarbonyl, cycloalkoxycarbonyl or

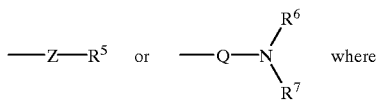

R$^5$ represents optionally substituted aryl or optionally substituted heterocyclyl,
Z represents a direct bond, or represents —CH$_2$—, O, S, SO, SO$_2$ or CO,
or represents —CO—O—, the oxygen atom being bonded to R$^5$,
or represents —SO$_2$—O—, the oxygen atom being bonded to R$^5$,
or represents —S—CH$_2$—SO$_2$—, the sulphur atom of the thio group being bonded to
R$^6$ and R$^7$ independently of one another represent hydrogen, alkyl, halogenoalkyl, alkoxyalkyl, alylcarbonyl, optionally substituted aryl, optionally substituted arylcarbonyl, optionally substituted arylsulphonyl, optionally substituted arylaminocarbonyl or optionally substituted arylmethylsulphonyl, or R$^6$ and R$^7$ together with the nitrogen atom to which they are bonded represent an optionally alkyl-substituted heterocyclic ring which can additionally contain an oxygen atom or an alkylimino group and
Q represents a direct bond or a carbonyl group, or
R$^1$ and R$^2$, or R$^2$ and R$^3$, or R$^3$ and R$^4$, in each case together, represent an optionally substituted alkylene chain having 3 or 4 members in which one or two (non-adjacent) carbon atoms can be replaced by oxygen atoms,
A represents one of the following groups —SO$_2$—R$^8$, —CO—R$^9$ or

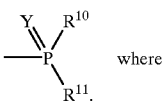

where

Y represents oxygen or sulphur and
R$^8$, R$^9$, R$^{10}$ and R$^{11}$ independently of one another represent alkyl, halogenoalkyl, alkoxy, halogenoalkoxy, alkylthio, halogenoalkyltio, alkenyl, halogenoalkenyl, alkenyloxy, alkenylthio, alkinyl, alkinyloxy, alkinylthio, amino, alkylamino, dialkylamino, optionally substituted aryl, optionally substituted aryloxy, optionally substituted arylthio, optionally substituted cycloalkyl, optionally substituted cycloalkyloxy, optionally substituted cycloalkylthio, optionally substituted cycloalkylamino, optionally substituted dicycloalkylamino or an optionally substituted saturated or unsaturated heterocyclic radical, or
R$^{10}$ and R$^{11}$ together with the phosphorus atom to which they are bonded represent an optionally substituted heterocyclic radical, and
X represents halogen,
and their acid addition salts and metal salt complexes.

Furthermore, it has been found that halogenobenzimidazoles of the formula (I) and their acid addition salts and metal salt complexes are obtained when
a) benzimidazole derivatives of the formula

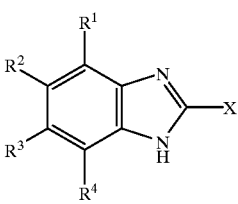

(II)

in which
R$^1$, R$^2$, R$^3$, R$^4$ and X have the abovementioned meanings, are reacted with halides of the formula

A—X$^1$ (III)

in which
A has the abovementioned meaning and
X$^1$ represents halogen,k
if appropriate in the presence of an acid-binding agent and if appropriate in the presence of a diluent,
and, if appropriate, the resulting compounds of the formula (I) are subjected to an addition reaction with an acid or a metal salt.

Finally, it has been found that the halogenobenzimidazoles of the formula (I) and their acid addition salts and metal salt complexes have very good microbicidal properties and can be employed both in crop protection and in the protection of materials.

Surprisingly, the substances according to the invention display a better fungicidal activity than 2-cyano-3-dimethylaminosulphonyl-6,6,7,7-tetrafluoro-[1,4]dioxino[2,3-f]benzimidazole and 2-cyano-6,6-difluoro-2-dimethylaminosulphonyl-[1,3]dioxolo[4,5-f]benzimidazole, which are prior-art active compounds of similar constitution and the same direction of action.

Formula (I) provides a general definition of the substances according to the invention.

$R^1$, $R^2$, $R^3$ and $R^4$ independently of one another preferably represent hydrogen fluorine, chlorine, bromine, iodine, cyano, nitro, straight-chain or branched alkyl having 1 to 8 carbon atoms, straight-chain or branched halogenoalkyl having 1 to 6 carbon atoms and 1 to 13 identical or different halogen atoms, straight-chain or branched alkoxy having 1 to 8 carbon atoms, straight-chain or branched halogenoalkoxy having 1 to 6 carbon atoms and 1 to 13 identical or different halogen atoms, straight-chain or branched alkylthio having 1 to 8 carbon atoms, straight-chain or branched halogenoalkylthio having 1 to 6 carbon atoms and 1 to 13 identical or different halogen atoms, straight-chain or branched allylsulphinyl having 1 to 8 carbon atoms, straight-chain or branched halogenoalkylsulphinyl having 1 to 6 carbon atoms and 1 to 13 identical or different halogen atoms, straight-chain or branched alkylsulphonyl having 1 to 8 carbon atoms, straight-chain or branched halogenoalkylsulphonyl having 1 to 6 carbon atoms and 1 to 13 identical or different halogen atoms, cycloalkyl having 3 to 6 carbon atoms which is optionally monosubstituted to pentasubstituted by identical or different substituents from the series consisting of halogen and/or alkyl having 1 to 4 carbon atoms, or represent hydroxycarbonyl, alkylcarbonyl having 1 to 6 carbon atoms in the straight-chain or branched all moiety, alkoxycarbonyl having 1 to 6 carbon atoms in the straight-chain or branched alkoxy moiety, cycloalkylcarbonyl having 3 to 6 carbon atoms in the cycloalkyl moiety, cycloalkoxycarbonyl having 3 to 6 carbon atoms in the cycloalkyl moiety, or represent —Z—$R^5$ or

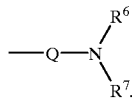

$R^5$ preferably represents aryl having 6 to 10 carbon atoms, it being possible for each of these radicals to be monosubstituted to trisubstituted by identical or different substituents from the series consisting of halogen, cyano, nitro, alkyl having 1 to 4 carbon atoms, alkoxy having 1 to 4 carbon atoms, alkylthio having 1 to 4 carbon atoms, halogenoalkyl having 1 to 4 carbon atoms and 1 to 5 identical or different halogen atoms, halogenoalkoxy having 1 to 4 carbon atoms and 1 to 5 identical or different halogen atoms, halogenoalkyltio having 1 to 4 carbon atoms and 1 to 5 identical or different halogen atoms, alkylsulphinyl having 1 to 4 carbon atoms, alkylsulphonyl having 1 to 4 carbon atoms, halogenoalkylsulphinyl having 1 to 4 carbon atoms and 1 to 5 identical or different halogen atoms and/or halogenoalkylsulphonyl having 1 to 4 carbon atoms and 1 to 5 identical or different halogen atoms.

$R^5$ preferably also represents an unsaturated heterocyclyl radical having 5 or 6 ring members and 1 to 3 heteroatoms, such as nitrogen, oxygen and/or sulphur, it being possible for these radicals to be monosubstituted to trisubstituted by identical or different substituents from the series consisting of halogen alkyl having 1 to 4 carbon atoms, alkoxy having 1 to 4 carbon atoms, halogenoalkyl having 1 to 4 carbon atoms and 1 to 5 identical or different halogen atoms, halogenoalkoxy having 1 to 4 carbon atoms and 1 to 5 identical or different halogen atoms, alkoxycarbonyl having 1 to 3 carbon atoms in the alkoxy moiety, cycloalkyl having 3 to 6 carbon atoms, cyano and/or nitro.

Z preferably also represents a direct bond, and —CH$_2$—, O, S, SO, SO$_2$ or CO,
or represents —CO—O—, the oxygen atom being bonded to $R^5$,
or represents —SO$_2$—O—, the sulphur atom being bonded to $R^5$,
or represents —S—CH$_2$—SO$_2$—, the sulphur atom of the thio group being bonded to $R^5$.

$R^6$ and $R^7$ independently of one another preferably represent hydrogen, straight-chain or branched alkyl having 1 to 6 carbon atoms, straight-chain or branched halogenoalkyl having 1 to 6 carbon atoms and 1 to 13 identical or different halogen atoms, straight-chain or branched alkoxyalkyl having 1 to 4 carbon atoms in the alkoxy moiety and 1 to 4 carbon atoms in the alkyl moiety, alkylcarbonyl having 1 to 6 carbon atoms in the straight-chain or branched alkyl moiety, aryl having 6 to 10 carbon atoms, arylcarbonyl having 6 to 10 carbon atoms in the aryl moiety, arylsulphonyl having 6 to 10 carbon atoms, arylaminocarbonyl having 6 to 10 carbon atoms in the aryl moiety, or arylmethylsulphonyl having 6 to 10 carbon atoms in the aryl moiety, it being possible for each of the abovementioned aryl radicals to be monosubstituted to trisubstituted by identical or different substituents from the series consisting of halogen, cyano, nitro, alkyl having 1 to 4 carbon atoms, alkoxy having 1 to 4 carbon atoms, alkylthio having 1 to 4 carbon atoms, halogenoalkyl having 1 to 4 carbon atoms and 1 to 5 identical or different halogen atoms, halogenoalkoxy having 1 to 4 carbon atoms and 1 to 5 identical or different halogen atoms, halogenoalkylthio having 1 to 4 carbon atoms and 1 to 5 identical or different halogen atoms, alkylsulphinyl having 1 to 4 carbon atoms, alkylsulphonyl having 1 to 4 carbon atoms, halogenoalkylsulphinyl having 1 to 4 carbon atoms and 1 to 5 identical or different halogen atoms and/or halogenoalkylsulphonyl having 1 to 4 carbon atoms and 1 to 5 identical or different halogen atoms.

$R^6$ and $R^7$ furthermore also together with the nitrogen atom to which they are bonded preferably represent a heterocyclic ring having 5 or 6 ring members which can additionally contain an oxygen atom or a $C_1$–$C_4$-alkylimino group and which is optionally monosubstituted to trisubstituted by alkyl having 1 to 4 carbon atoms.

Q also preferably represents a direct bond or a carbonyl group.

$R^1$ and $R^2$, or $R^2$ and $R^3$, or $R^3$ and $R^4$ in each case together also preferably represent an alkylene chain having 3 or 4 members in which one or two (non-adjacent) carbon atoms can be replaced by oxygen atoms and which is optionally monosubstituted or hexasubstituted by halogen, alkyl having 1 to 4 carbon atoms and/or halogenoalkyl having 1 to 4 carbon atoms and 1 to 9 halogen atoms.

X preferably represents fluorine, chlorine, bromine or iodine.

A also preferably represents one of the groups —SO$_2$—R$^8$, —CO—R$^9$ or

Y also preferably represents oxygen or sulphur.

R$^8$, R$^9$, R$^{10}$ and R$^{11}$ independently of one another preferably represent straight-chain or branched alkyl having 1 to 4 carbon atoms, straight-chain or branched halogenoalkyl having 1 to 4 carbon atoms and 1 to 5 identical or different halogen atoms, straight-chain or branched alkoxy having 1 to 4 carbon atoms, straight-chain or branched halogenoalkoxy having 1 to 4 carbon atoms and 1 to 5 identical or different halogen atoms, straight-chain or branched alkylthio having 1 to 4 carbon atoms, straight-chain or branched halogenoalkylthio having 1 to 4 carbon atoms and 1 to 5 identical or different halogen atoms, straight-chain or branched alkenyl having 2 to 4 carbon toms, straight-chain or branched halogenoalkenyl having 2 to 4 carbon atoms and 1 to 5 identical or different halogen atoms, straight-chain or branched alkenyloxy having 2 to 4 carbon atoms, straight-chain or branched alkenylthio having 2 to 4 carbon atoms, straight-chain or branched alkinyl having 2 to 4 carbon atoms, straight-chain or branched aLkinyloxy having 2 to 4 carbon atoms, straight-chain or branched alkinylthio having 2 to 4 carbon atoms, amino, alkylamino having 1 to 4 carbon atoms, dialkylamino having 1 to 4 carbon atoms in each alkyl moiety, or represents phenyl, phenoxy or phenylthio, it being possible for each of these radicals to be monosubstituted to trisubstituted by identical or different substituents from the series consisting of fluorine, chlorine, bromine, nitro, alkyl having 1 to 4 carbon atoms, halogenoalkyl having 1 to 4 carbon atoms and 1 to 5 fluorine, chlorine and/or bromine atoms, alkoxy having 1 to 4 carbon atoms and/or halogenoalkoxy having 1 to 4 carbon atoms and 1 to 5 fluorine, chlorine and/or bromine atoms, or represents cycloalkyl having 3 to 7 carbon atoms, cycloalkyloxy having 3 to 7 carbon atoms, cycloalkylthio having 3 to 7 carbon atoms, cycloalkylamino having 3 to 7 carbon atoms, pyrrolidinyl, piperidinyl or morpholinyl, it being possible for each of these abovementioned radicals to be monosubstituted to trisubstituted by identical or different substituents from the series consisting of fluorine, chlorine, bromine, alkyl having 1 to 4 carbon atoms and/or halogenoalkyl having 1 to 4 carbon atoms and 1 to 5 fluorine, chlorine and/or bromine atoms, or represents an unsaturated heterocyclyl radical having 5 or 6 ring members and 1 to 3 heteroatoms, such as nitrogen, oxygen and/or sulphur, it being possible for these radicals to be monosubstituted to trisubstituted by identical or different substituents from the series consisting of halogen, cyano, nitro, hydroxyl, amino, formyl, carboxyl, carbamoyl, thiocarbamoyl, alkyl having 1 to 4 carbon atoms, alkoxy having 1 to 4 carbon atoms, halogenoalkyl having 1 to 4 carbon atoms and 1 to 5 identical or different halogen atoms, halogenoalkoxy having 1 to 4 carbon atoms and 1 to 5 identical or different halogen atoms, alkoxycarbonyl having 1 to 4 carbon atoms in the alkoxy moiety, cycloalkyl having 3 to 6 carbon atoms, halogenoalkylsulphinyl having 1 to 4 carbon atoms and 1 to 5 identical or different halogen atoms, halogenoalkylsulphonyl having 1 to 4 carbon atoms and 1 to 5 identical or different halogen atoms, alkylamino having 1 to 4 carbon atoms, hydroxyalkylamino having 1 to 4 carbon atoms, dialkylamino having 1 to 4 carbon atoms in each alkyl group, alkylcarbonyl having 1 to 4 carbon atoms in the alkyl moiety, hydroximinoalkyl having 1 to 4 carbon atoms in the alkyl moiety, alkoximinoalkyl having 1 to 4 carbon atoms in the alkoxy moiety and 1 to 4 carbon atoms in the alkyl moiety, alkylcarbonyloxy having 1 to 4 carbon atoms in the alkyl moiety and/or halogenoalkylcarbonyloxy having 1 to 4 carbon atoms in the halogenoalkyl group and 1 to 5 identical or different halogen atoms.

R$^{10}$ and R$^{11}$ furthermore together with the phosphorus atom to which they are bonded preferably represent a 5- or 6-membered heterocyclyl radical which can contain one or two further heteroatoms, such as oxygen, sulphur and/or nitrogen, and which can be monosubstituted to trisubstituted by identical or different substituents from the series consisting of fluorine, chlorine, bromine, alkyl having 1 to 4 carbon atoms, alkoxy having 1 to 4 carbon atoms and/or halogenoalkoxy having 1 to 4 carbon atoms and 1 to 5 fluorine, chlorine and/or bromine atoms.

R$^1$, R$^2$, R$^3$ and R$^4$ independently of one another particularly preferably represent hydrogen, fluorine, chlorine, bromine, iodine, cyano, nitro, straight-chain or branched alkyl having 1 to 6 carbon atoms, halogenoalkyl having 1 or 2 carbon atoms and 1 to 5 fluorine, chlorine and/or bromine atoms, straight-chain or branched alkoxy having 1 to 6 carbon atoms, halogenoalkyl having 1 or 2 carbon atoms and 1 to 5 fluorine, chlorine and/or bromine atoms, straight-chain or branched alkylthio having 1 to 6 carbon atoms, halogenoalkylthio having 1 or 2 carbon atoms and 1 to 5 fluorine, chlorine and/or bromine atoms, straight-chain or branched alkylsulphinyl having 1 to 6 carbon atoms, halogenoalkylsulphinyl having 1 or 2 carbon atoms and 1 to 5 fluorine, chlorine and/or bromine atoms, straight-chain or branched alkylsulphonyl having 1 to 6 carbon atoms, halogenoalkylsulphonyl having 1 or 2 carbon atoms and 1 to 5 fluorine, chlorine and/or bromine atoms, cycloalkyl having 3 to 6 carbon atoms which is optionally monosubstituted to trisubstituted by identical or different substituents from the series consisting of fluorine, chlorine, bromine, methyl and/or ethyl, or represent hydroxycarbonyl, alkylcarbonyl having 1 to 4 carbon atoms in the straight-chain or branched allyl moiety, alkoxycarbonyl having 1 to 4 carbon atoms in the straight-chain or branched alkoxy moiety, cycloalkylcarbonyl having 3 to 6 carbon atoms in the cycloalkyl moiety, cycloalkoxycarbonyl having 3 to 6 carbon atoms in the cycloalkyl moiety, or represent —Z—R$^5$ or

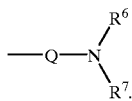

R⁵ particularly preferably represents phenyl which can be monosubstituted to trisubstituted by identical or different substituents from the series consisting of fluorine, chlorine, bromine, cyano, nitro, methyl, ethyl, methoxy, ethoxy, methylthio, ethylthio, halogenoalkyl having 1 or 2 carbon atoms and 1 to 5 fluorine, chlorine and/or bromine atoms, halogenoalkoxy having 1 or 2 carbon atoms and 1 to 5 fluorine, chlorine and/or bromine atoms, halogenoalkylthio having 1 or 2 carbon atoms and 1 to 5 fluorine, chlorine and/or bromine atoms, methylsulphinyl, ethylsulphinyl, methylsulphonyl, ethylsulphonyl, halogenoalkylsulphinyl having 1 or 2 carbon atoms and 1 to 5 fluorine, chlorine and/or bromine atoms and/or halogenoalkylsulphonyl having 1 or 2 carbon atoms and 1 to 5 fluorine, chlorine and/or bromine atoms.

R⁵ also particularly preferably represents an unsaturated heterocyclyl radical having 5 or 6 ring members and 1 to 3 heteroatoms, such as nitrogen, oxygen and/or sulphur, it being possible for each of these radicals to be monosubstituted or disubstituted by identical or different substituents from the series consisting of fluorine, chlorine, bromine, methyl, ethyl, methoxy, ethoxy, halogenoalkyl having 1 or 2 carbon atoms and 1 to 5 fluorine, chlorine and/or bromine atoms, halogenoalkoxy having 1 or 2 carbon atoms and 1 to 5 fluorine, chlorine and/or bromine atoms, methoxycarbonyl, ethoxycarbonyl, cycloalkyl having 3 to 6 carbon atoms, cyano and/or nitro.

Z also particularly preferably represents a direct bond, and also represents $CH_2$, O, S, SO, $SO_2$ or CO,
or represents —CO—O—, the oxygen atom being bonded to R⁵,
or represents —$SO_2$—O—, the sulphur atom being bonded to R⁵,
or represents —S—$CH_2$—$SO_2$—, the sulphur atom of the thio group being bonded to R⁵.

R⁶ and R⁷ independently of one another particularly preferably represent hydrogen straight-chain or branched alkyl having 1 to 4 carbon atoms, halogenoalkyl having 1 or 2 carbon atoms and 1 to 5 fluorine, chlorine and/or bromine atoms, straight-chain or branched alkoxyalkyl having 1 to 3 carbon atoms in the alkoxy moiety and 1 to 3 carbon atoms in the alkyl moiety, alkylcarbonyl having 1 to 4 carbon atoms in the straight-chain or branched alkyl moiety, phenyl, phenylcarbonyl, phenylsulphonyl, phenylaminocarbonyl or phenylmethylsulphonyl, it being possible for each of the abovementioned phenyl radicals to be monosubstituted to trisubstituted by identical or different substituents from the series consisting of fluorine, chlorine, bromine, cyano, nitro, alkyl having 1 or 2 carbon atoms, alkoxy having 1 or 2 carbon atoms, alkylthio having 1 or 2 carbon atoms, halogenoalkyl having 1 or 2 carbon atoms and 1 to 5 fluorine, chlorine and/or bromine atoms, halogenoalkoxy having 1 or 2 carbon atoms and 1 to 5 fluorine, chlorine and/or bromine atoms, halogenoalkylthio having 1 or 2 carbon atoms and 1 to 5 fluorine, chlorine and/or bromine atoms, alkylsulphinyl having 1 or 2 carbon atoms, alkylsulphonyl having 1 or 2 carbon atoms, halogenoalkylsulphinyl having 1 or 2 carbon atoms and 1 to 5 fluorine, chlorine and/or bromine atoms and/or halogenoalkylsulphonyl having 1 or 2 carbon atoms and 1 to 5 fluorine, chlorine and/or bromine atoms.

R⁶ and R⁷ furthermore also together with the nitrogen atom to which they are bonded particularly preferably represent a saturated heterocyclic ring having 5 or 6 ring members which is optionally monosubstituted to trisubstituted by methyl and/or ethyl, it being possible for a carbon atom of the ring to be replaced by oxygen or methylimino.

Q also particularly preferably represents a direct bond or a carbonyl group.

R¹ and R², or R² and R³, or R³ and R⁴, in each case together also particularly preferably represent an alkylene chain having 3 or 4 members which is optionally monosubstituted to trisubstituted by fluorine, chlorine, methyl and/or trifluoromethyl and in which one or two (non-adjacent) carbon atoms can be replaced by oxygen.

X also particularly preferably represents fluorine, chlorine, bromine or iodine.

A also particularly preferably represents one of the groups —$SO_2$—R⁸, —CO—R⁹ or

Y also particularly preferably represents oxygen or sulphur.

R⁸, R⁹, R¹⁰ and R¹¹ independently of one another particularly preferably represent methyl, ethyl, n- or i-propyl, n-, i-, s- or t-butyl, trifluoromethyl, trifluoroethyl, methoxy, ethoxy, n- or i-propoxy, n-, i-, s- or t-butoxy, difluoromethoxy, trifluoromethoxy, difluorochloromethoxy, trifluoroethoxy, methylthio, ethylthio, n- or i-propylthio, difluoromethylthio, trifluoromethylthio, difluorochloromethylthio, allyl, n- or s-butenyl; allyloxy, n- or s-butenyloxy; allylthio, n- or s-butenylthio; propargyl, n- or s-butinyl; propargyloxy; propargylthio; amino; methylamino, ethylamino, n- or i-propylamino, n-, i-, s- or t-butylamino; dimethylamino, diethylamino, di-n- or i-propylamino, methylethylamino, methyl-n- or i-propylamino;
or represent phenyl, phenoxy or phenylthio, it being possible for each of these radicals to be monosubstituted to trisubstituted by identical or different substituents from the series consisting of fluorine, chlorine, bromine, nitro, methyl, ethyl, n- or i-propyl, methoxy, ethoxy, n- or i-propoxy, trifluoromethyl and/or trifluoromethoxy;
or represent cyclopropyl, cyclopentyl, cyclohexyl, cyclopropyloxy, cyclopentyloxy, cyclohexyloxy, cyclopropylthio, cyclopentylthio, cyclohexylthio, cyclopropylamino, cyclopentylamino, cyclohexylamino, 1-pyrrolidinyl, 1-piperidinyl, and 1-morpholinyl, it being possible for each of these radicals to be monosubstituted to trisubstituted by identical or different substituents from the series consisting of fluorine, chlorine, bromine, methyl, ethyl, n- or i-propyl and/or trifluoromethyl,
or represents an unsaturated heterocyclyl radical having 5 or 6 ring members and 1 to 3 heteroatoms, such as nitrogen, oxygen and/or sulphur, it being possible for each of these radicals to be monosubstituted or disubstituted by identical or different substituents from the series consisting of fluorine, chlorine, bromine, cyano, nitro, hydroxyl, amino, formyl, carboxyl, carbamoyl, thiocarbamoyl, alkyl having 1 to 4 carbon atoms, alkoxy having 1 to 4 carbon atoms, halogenoalkyl having 1 or 2 carbon atoms and 1 to 5 fluorine, chlorine and/or bromine atoms, halogenoalkoxy having 1 or 2 carbon atoms and 1 to 5 fluorine, chlorine and/or bromine atoms, alkoxycarbonyl having 1 or 2 carbon atoms in the alkoxy moiety, cycloalkyl having 3 to 6 carbon atoms, halogenoalkylsulphinyl having 1 or 2 carbon atoms and 1 to 5 fluorine, chlorine and/or bromine atoms, halogenoalkylsulphonyl having 1 or 2 carbon atoms and 1 to 5 fluorine, chlorine and/or bromine atoms, alkylamino having 1 or 2 carbon atoms, hydroxyalkylamino having 1 or 2 carbon atoms, dialkylamino having 1 or 2 carbon atoms in each allyl group, alkylcarbonyl having 1 or 2 carbon atoms in the alkyl moiety, hydroximinoalkyl having 1 or 2 carbon atoms in the alkyl moiety, alkoximinoalkyl having 1 or 2 carbon atoms in the alkoxy moiety and 1 or 2 carbon atoms in the alkyl moiety, alkylcarbonyloxy having 1 or 2 carbon atoms in the alkyl group and/or halogenoalkylcarbonyloxy having 1 or 2 carbon atoms in the halogenoalkyl group and 1 to 5 fluorine, chlorine and/or bromine atoms.

$R^{10}$ and $R^{11}$ furthermore together with the phosphorus atom to which they are bonded particularly preferably represent a 5- or 6-membered heterocyclyl radical which can contain one or two further heteroatoms, such as oxygen, sulphur and/or nitrogen, and which can be monosubstituted to trisubstituted by identical or different substituents from the series consisting of methyl, ethyl, n- or i-propyl, methoxy, ethoxy, n- or i-propoxy, chlorine and/or trifluoromethyl.

$R^1$, $R^2$, $R^3$ and $R^4$ independently of one another very particularly preferably represent hydrogen, fluorine, chlorine, bromine, cyano, nitro, or represent methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl, ethylsulphonyl, trifluoromethyl, difluoromethoxy, trifluoromethoxy, difluoromethylthio, trifluoromethylthio, trifluoromethylsulphinyl, trifluoromethylsulphonyl, acetyl, acetyloxy, methoxycarbonyl, ethoxycarbonyl, cyclopropyl, cyclohexyl, or represent Z—$R^5$ or

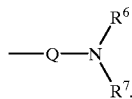

$R^5$ very particularly preferably represents phenyl which can be monosubstituted to trisubstituted by identical or different substituents from the series consisting of fluorine, chlorine, bromine, cyano, nitro, or represents methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl, ethylsulphonyl, trifluoromethyl, difluoromethoxy, trifluoromethoxy, difluoromethylthio, trifluoromethylthio, difluoromethylsulphinyl and/or trifluoromethylsulphonyl.

$R^5$ also very particularly preferably represents pyrrolyl, furyl, thienyl, pyrazolyl, imidazolyl, thiazolyl, isothiazolyl, oxazolyl, isoxazolyl, oxadiazolyl, thiadiazolyl, 1,2,3-triazinyl, 1,2,4triazinyl, 1,3,5-triazinyl, pyridinyl, pyrimidinyl, pyrazinyl or pyridazinyl, it being possible for each of these radicals to be monosubstituted or disubstituted by identical or different substituents from the series consisting of fluorine, chlorine, methyl, methoxy, trifluoromethyl, trifluoromethoxy and/or trifluoroethoxy.

Z also very particularly preferably represents a direct bond, or represents $CH_2$, O, S, SO, $SO_2$, CO,
or represents —CO—O—, the oxygen atom being bonded to $R^5$,
or represents —$SO_2$—O—, the sulphur atom being bonded to $R^5$,
or represents —S—$CH_2$—$SO_2$—, the sulphur atom of the thio group being bonded to $R^5$.

$R^6$ and $R^7$ independently of one another very particularly preferably represent hydrogen methyl, ethyl, n-propyl, isopropyl or phenyl.

$R^6$ and $R^7$ furthermore also together with the nitrogen atom to which they are bonded very particularly preferably represent pyrrolidinyl, piperidinyl, morpholinyl or 4-methylpiperazinyl.

Q also very particularly preferably represents a direct bond or a carbonyl group.

$R^1$ and $R^2$, or $R^2$ and $R^3$, or $R^3$ and $R^4$, in each case together, also very particularly preferably represent the groups —$CF_2$—O—$CF_2$—, —O—$CF_2$—O—, —O—$CF_2$—CHF—O—, —O—CF—CHF—O—, —O—$CF_2$—$CF_2$—O—, —O—$CF_2$—CFCl—O— or —O—CFCl—CFCl—O—.

X also very particularly preferably represents fluorine, chlorine, bromine or iodine.

A also very particularly preferably represents one of the groups —$SO_2$—$R^8$, —CO—$R^9$ or

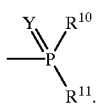

Y also very particularly preferably represents oxygen or sulphur.

$R^8$, $R^9$, $R^{10}$ and $R^{11}$ independently of one another particularly preferably represent methyl, ethyl, n- or i-propyl, n-, i-, s- or t-butyl, trifluoromethyl, trifluoroethyl, methoxy, ethoxy, n- or i-propoxy, n-, i-, s- or t-butoxy, difluoromethoxy, trifluoromethoxy, difluorochloromethoxy, trifluoroethoxy, methylthio, ethylthio, n- or i-propylthio, difluoromethylthio, trifluoromethylthio, difluorochloromethylthio, allyl, n- or s-butenyl; allyloxy, n- or s-butenyloxy; allylthio, n- or s-butenylthio; propargyl, n- or s-butinyl; propargyloxy; propargylthio; amino; methylamino, ethylamino, n- or i-propylamino, n-, i-, s- or t-butylamino; dimethylamino, diethylamino, di-n- or i-propylamino, methylethylamino, methyl-n- or i-propylamino;
or represent phenyl, phenoxy or phenylthio, it being possible for each of these radicals to be monosubstituted to trisubstituted by identical or different substituents from the series consisting of fluorine, chlorine, bromine, nitro, methyl, ethyl, n- or i-propyl, methoxy, ethoxy, n- or i-propoxy, trifluoromethyl and/or trifluoromethoxy;

or represent cyclopropyl, cyclopentyl, cyclohexyl, cyclopropyloxy, cyclopentyloxy, cyclohexyloxy, cyclopropylthio, cyclopentylthio, cyclohexylthio, cyclopropylamino, cyclopentylamino, cyclohexylamino, 1-pyrrolidinyl, 1-piperidinyl, and 1-morpholinyl, it being possible for each of these radicals to be monosubstituted to trisubstituted by identical or different substituents from the series consisting of fluorine, chlorine, bromine, methyl, ethyl, n- or i-propyl and/or trifluoromethyl, or represent pyrrolyl, furyl, thienyl, pyrazolyl, imidazolyl, thiazolyl, isothiazolyl, oxazolyl, isoxazolyl, oxadiazolyl, thiadiazolyl, 1,2,3-triazinyl, 1,2,4-triazinyl, 1,3,5-triazinyl, pyridinyl, pyrimidinyl, pyrazinyl or pyridazinyl, it being possible for each of these radicals to be monosubstituted or disubstituted by identical or different substituents from the series consisting of fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl, ethylsulphonyl, trifluoromethyl, difluoromethoxy, trifluoromethoxy, difluoromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroxyiminomethyl, hydroxyiminoethyl, methoxyiminomethyl, ethoxyiminomethyl, methoxyiminoethyl and/or ethoxyiminoethyl.

$R^{10}$ and $R^{11}$ furthermore also together with the phosphorus atom to which they are bonded very particularly preferably represent a 5- or 6-membered heterocyclyl radical which can contain one or two further heteroatoms, such as oxygen, sulphur and/or nitrogen, and which can be monosubstituted to trisubstituted by identical or different substituents from the series consisting of methyl, ethyl, n- or i-propyl, methoxy, ethoxy, n- or i-propoxy, chlorine and/or trifluoromethyl.

The definitions of radicals given above, in general or in preferred ranges, apply to the end products of the formula (I) and, analogously, to the starting materials or intermediates required in each case for the preparation.

Other preferred compounds according to the invention are addition products of acids and those halogenobenzimidazoles of the formula (I) in which $R^1$, $R^2$, $R^3$, $R^4$, A and X have those meanings which have been mentioned as being preferred for these radicals.

The acids which can be subjected to the addition reaction preferably include hydrohalic acids, such as, for example, hydrochloric acid and hydrobromic acid, in particular hydrochloric acid, furthermore phosphoric acid, sulphuric acid, nitric acid, mono- and bifunctional carboxylic acid and hydroxycarboxylic acids, such as, for example, acetic acid, maleic acid, succinic acid, fumaric acid, tartaric acid, citric acid, salicylic acid, sorbic acid and lactic acid, and also sulphonic acids, such as, for example, p-toluenesulphonic acid, 1,5-naphthalenedisulphonic acid, saccharine and thiosaccharine.

Other preferred compounds according to the invention are addition products of salts of metals of main groups II to IV and subgroups I and II and also IV to VIII of the Periodic Table of the Elements and those halogenobenzimidazoles of the formula (I) in which $R^1$, $R^2$, $R^3$, $R^4$, A and X have those meanings which have been mentioned as being preferred for these radicals.

Particularly preferred in this context are salts of copper, zinc, manganese, magnesium, tin, iron and of nickel. Suitable anions of these salts are those which are derived from those acids which lead to physiologically acceptable addition products. Particularly preferred acids of this type are, in this context, the hydrohalic acids, such as, for example, hydrochloric acid and hydrobromic acid, furthermore phosphoric acid, nitric acid and sulphuric acid.

Examples of substances according to the invention which may be mentioned are the halogenobenzimidazoles listed in the tables which follow:

TABLE 1

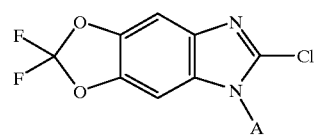

where A represents the following substituents:

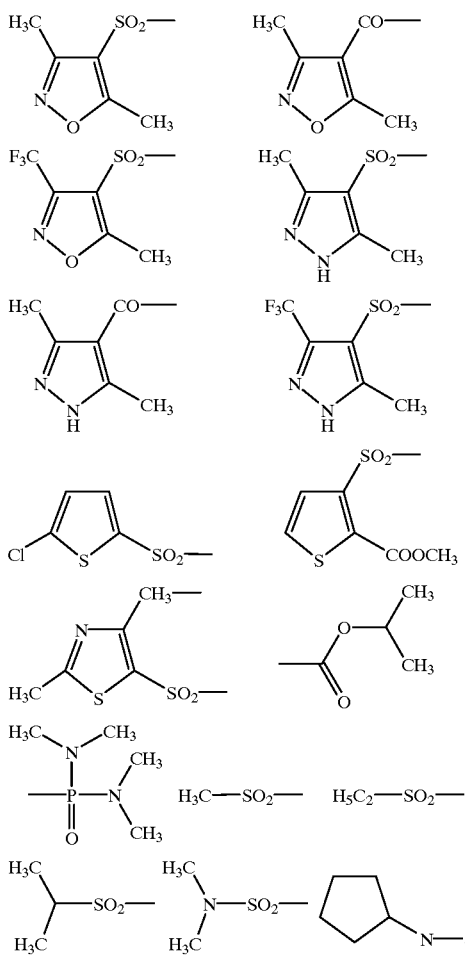

-continued

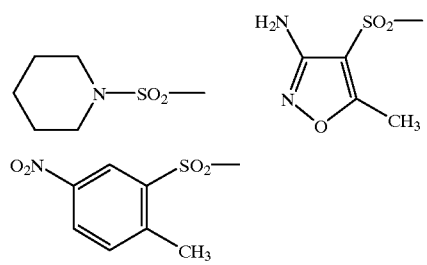

TABLE 2

(Ib)

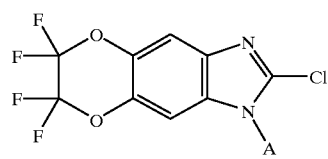

where A represents the substituents mentioned in Table 1.

TABLE 3

(Ic)

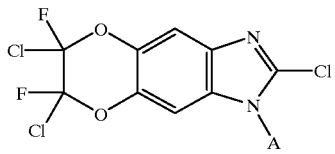

where A represents the substituents mentioned in Table 1.

TABLE 4

(Id)

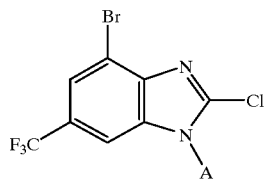

where A represents the substituents mentioned in Table 1.

TABLE 5

(Ie)

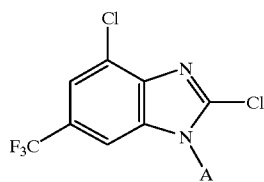

where A represents the substituents mentioned in Table 1.

TABLE 6

(If)

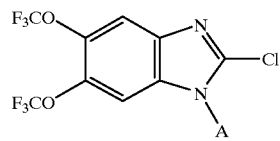

where A represents the substituents mentioned in Table 1.

TABLE 7

(Ig)

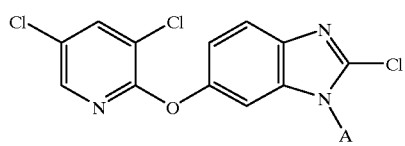

where A represents the substituents mentioned in Table 1.

TABLE 8

(Ih)

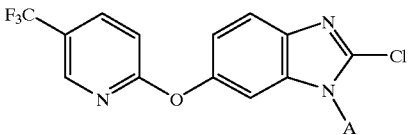

where A represents the substituents mentioned in Table 1.

TABLE 9

(Ii)

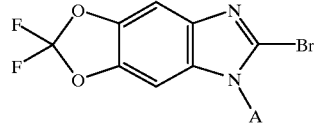

where A represents the substituents mentioned in Table 1.

TABLE 10

(Ij)

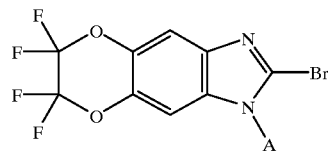

where A represents the substituents mentioned in Table 1.

TABLE 11

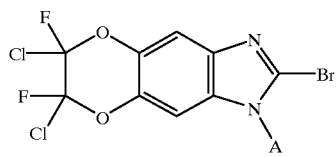

(Ik)

where A represents the substituents mentioned in Table 1.

TABLE 12

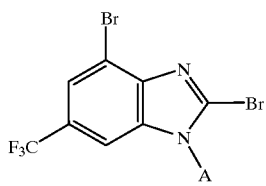

(Il)

where A represents the substituents mentioned in Table 1.

TABLE 13

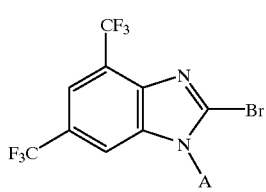

(Im)

where A represents the substituents mentioned in Table 1.

TABLE 14

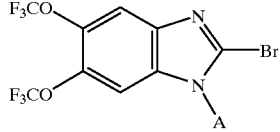

(In)

where A represents the substituents mentioned in Table 1.

TABLE 15

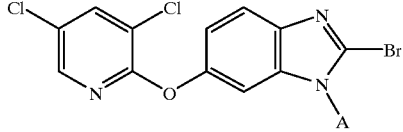

(Io)

where A represents the substituents mentioned in Table 1.

TABLE 16

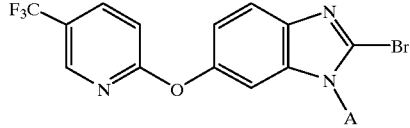

(Ip)

where A represents the substituents mentioned in Table 1.

If 2-chloro-1H-benzimidazole and toluene-4-sulphonyl chloride are used as starting substances, the course of process a) according to the invention can be illustrated by the following equation:

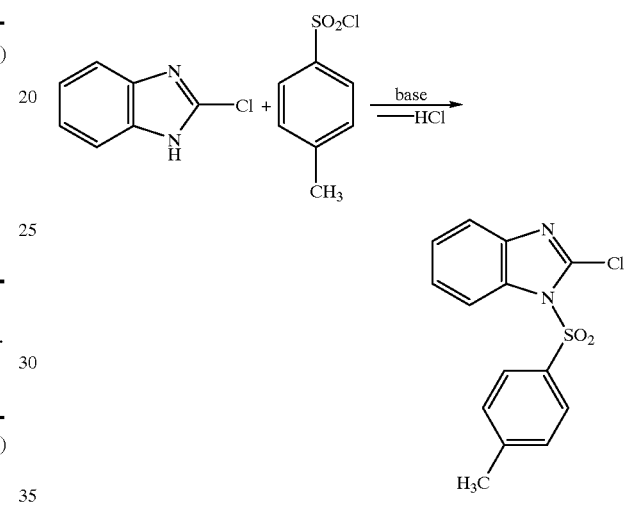

Formula (II) provides a general definition of the benzimidazole derivatives required as starting substances for carrying out process (a) according to the invention. In this formula (II), $R^1$, $R^2$, $R^3$, $R^4$ and X preferably, or in particular, have those meanings which have already been mentioned in connection with the description of the compounds of the formula (I) according to the invention as being preferred, or particularly preferred, for $R^1$, $R^2$, $R^3$, $R^4$ and X.

Some of the benzimidazole derivatives of the formula (II) are known (compare Chem. Pharm. Bull. 1981, 29, 2403; Synthesis 1988, 767; J. Chem. Soc. 1922, 947; WO-A 9408456; WO-A 9207867 Bull. Soc. Chim. Fr. 1988, 1, 139–142; EP-A 308918; J. C. S. Chem Com. 1976, 430; Liebigs Ann. Chem 1961, 649, 114 and J. Prakt. Chem 1965 28, 297).

The benzimidazole derivatives of the formula

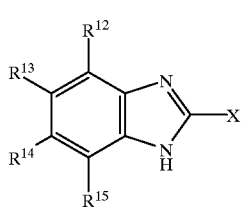

(IIa)

in which $R^{12}$, $R^{13}$, $R^{14}$ and $R^{15}$ independently of one another represent hydrogen, halogenoalkoxy or halogenoalkylthio, at least one of the radicals mentioned representing halogenoalkoxy or halogenoalkylthio, or $R^{12}$ and $R^{13}$, or $R^{13}$ and $R^{14}$, or $R^{14}$ and $R^{15}$, in each case together with the carbon atoms to which they are bonded form a five- or six-membered heterocyclic ring which has one or two (non-adjacent) oxygen atoms and which is at least monosubstituted by halogen and X represents halogen, are new.

Benzimidazole derivatives of the formula (IIa) can be prepared by (b) reacting benzimidazoles of the formula

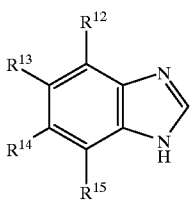

(IV)

in which $R^{12}, R^{13}, R^{14}$ and $R^{15}$ have the abovementioned meanings with, halogenating agents, if appropriate in the presence of a diluent and if appropriate in the presence of an acid-binding agent, or c) reacting bromobenzimidazoles of the formula

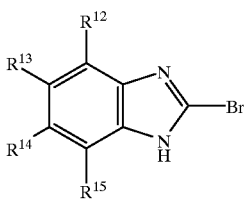

(IIb)

in which $R^{12}, R^{13}, R^{14}$ and $R^{15}$ have the abovementioned meanings with hydrofluoric, hydrochloric or hydriodic acid or with a salt of the formula $$M^+X^{2-}$$ (V)

in which

M represents a metal equivalent or a quaternary ammonium, sulphonium, sulphoxonium or phosphonium ion and $X^2$ represents fluorine, chlorine or iodine, if appropriate in the presence of a diluent.

Formula (IIa) provides a general definition of the new benzimidazole derivatives.

$R^{12}$, $R^{13}$, $R^{14}$ and $R^{15}$ independently of one another preferably represent hydrogen straight-chain or branched halogenoalkoxy having 1 to 6 carbon atoms and 1 to 13 identical or different halogen atoms, straight-chain or branched halogenoalkylthio having 1 to 6 carbon atoms and 1 to 13 identical or different halogen atoms, at least one of the radicals mentioned representing halogenoalkoxy or halogenoalkylthio.

$R^{12}$ and $R^{13}$, or $R^{13}$ and $R^{14}$, or $R^{14}$ and $R^{15}$, in each case together with the carbon atoms to which they are bonded, also preferably represent a five- or six-membered heterocyclic ring having one or two (non-adjacent) oxygen atoms which is monosubstituted to tetrasubstituted by halogen.

X preferably represents fluorine, chlorine, bromine or iodine.

$R^{12}$, $R^{13}$, $R^{14}$ and $R^{15}$ independently of one another particularly preferably represent hydrogen, difluromethoxy, trifluoromethoxy, difluorochloromethoxy, difluorobromomethoxy, trifluoroethoxy, difluoromethylthio, trifluoromethylthio, difluorochloromethylthio or difluorobromomethylthio, at least one of the radicals being other than hydrogen $R^{12}$ and $R^{13}$, or $R^{13}$ and $R^{14}$, or $R^{14}$ and $R^{15}$, in each case together with the carbon atoms to which they are bonded, also particularly preferably form a five- or six-membered, heterocyclic ring having one or two (non-adjacent) oxygen atoms which is monosubstituted to tetrasubstituted by fluorine, chlorine and/or bromine.

X also particularly preferably represents fluorine, chlorine, bromine or iodine.

If 5-trifluoromethoxy-1H-benzimidazole and N-bromosuccinimide are used as starting substances, the course of process (b) according to the invention can be illustrated by the following equation:

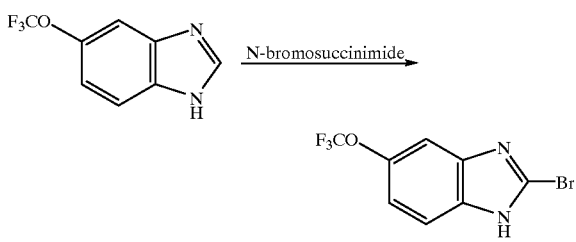

Formula (IV) provides a general definition of the benzimidazoles required as starting substances for carrying out process (b) according to the invention. In this formula, $R^{12}$, $R^{13}$, $R^{14}$ and $R^{15}$ preferably, or in particular, have those meanings which have already been given in connection with the description of the compounds of the formula (IIa) as being preferred, or particularly preferred, for $R^{12}$, $R^{13}$, $R^{41}$ and $R^{15}$.

Some of the benzimidazoles of the formula (IV) are known. 5-Pentafluoroethoxy-1H-benzimidazole, for example, has already been described (cf. Biomed. Environ. Mass Spectrom (1989), 18(10), 872–877).

The benzimidazoles of the formula

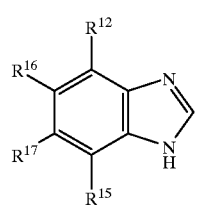

(IVa)

in which $R^{12}$ represents hydrogen, halogenoalkoxy or halogenoalkylthio, $R^{15}$ represents hydrogen halogenoalkoxy or halogenoalkylthio, $R^{16}$ represents hydrogen halogenoalkylthio or halogenoalkoxy, with the exception of pentafluoroethoxy, $R^{17}$ represents hydrogen, halogenoalkylthio or halogenoalkoxy, with the exception of pentafluoroethoxy, but where at least one of the radicals $R^{12}$, $R^{15}$, $R^{16}$ and $R^{17}$ is other than hydrogen, or $R^{12}$ and $R^{16}$, or $R^{16}$ and $R^{17}$, or $R^{17}$ and $R^{15}$, in each case together with the carbon atoms to which they are bonded, form a five- or six-membered heterocyclic ring having one or 2 (non-adjacent) oxygen atoms which is at least monosubstituted by halogen are new.

The benzimidazoles of the formula (IVa) can be prepared by d) reacting phenylenediamines of the formula

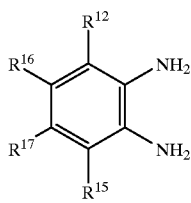

(IV)

in which $R^{12}$, $R^{15}$, $R^{16}$ and $R^{17}$ have the abovementioned meanings with formic acid, with one of its salts, or with one of its derivatives, such as, for example, formamide, trimethyl orthoformate, dialkylformamide acetate, formamide, s-triazine or carbon monoxide, at a temperature of from 0° C. to 180° C., preferably from 20° C. to 150° C., if appropriate in the presence of a diluent, such as, for example, water, methanol, ethanol or methoxyethanol.

Formula (IV-a) provides a general definition of the new benzimidazoles.

$R^{12}$ preferably represents hydrogen, straight-chain or branched halogenoalkoxy having 1 to 6 carbon atoms and 1 to 13 identical or different halogen atoms, or represents straight-chain or branched halogenoalkylthio having 1 to 6 carbon atoms and 1 to 13 identical or different halogen atoms.

$R^{15}$ preferably represents hydrogen, straight-chain or branched halogenoalkoxy having 1 to 6 carbon atoms and 1 to 13 identical or different halogen atoms, or represents straight-chain or branched halogenoalkylthio having 1 to 6 carbon atoms and 1 to 13 identical or different halogen atoms.

$R^{16}$ preferably represents hydrogen, straight-chain or branched halogenoalkylthio having 1 to 6 carbon atoms and 1 to 13 identical or different halogen atoms, or represents straight-chain or branched halogenoalkoxy having 1 to 6 carbon atoms and 1 to 13 identical or different halogen atoms, but with the exception of pentafluoroethoxy.

$R^{17}$ preferably represents hydrogen straight-chain or branched halogenoalkoxy having 1 to 6 carbon atoms and 1 to 13 identical or different halogen atoms, or represents straight-chain or branched halogenoalkoxy having 1 to 6 carbon atoms and 1 to 13 identical or different halogen atoms, but with the exception of pentafluoroethoxy.

However, one of the radicals $R^{12}$, $R^{15}$, $R^{16}$ and $R^{17}$ must be other than hydrogen.

$R^{12}$ and $R^{16}$, or $R^{16}$ and $R^{17}$, or $R^{17}$ and $R^{15}$, can, in each case, together with the carbon atoms to which they are bonded, also preferably form a five- or six-membered heterocyclic ring having one or two (non-adjacent) oxygen atoms which is monosubstituted to tetrasubstituted by halogen.

$R^{12}$, $R^{15}$, $R^{16}$ and $R^{17}$ independently of one another particularly preferably represent hydrogen, difluoromethoxy, trifluoromethoxy, difluoromethoxy, difluorobromomethoxy, trifluoroethoxy, difluoromethylthio, trifluoromethylthio, difluoromethylthio or difluorobromomethylthio, at least one of the radicals being other than hydrogen.

$R^{12}$ and $R^{16}$, or $R^{16}$ and $R^{17}$, or $R^{17}$ and $R^{15}$, in each case together with the carbon atoms to which they are bonded, also particularly preferably form a five- or six-membered heterocyclic ring having one or two (non-adjacent) oxygen atoms which is monosubstituted to tetrasubstituted by fluorine, chlorine and/or bromine.

If 4-trifluoromethoxy-o-phenylenediamine and formic acid are used as starting substances, the course of process (d) according to the invention can be illustrated by the following equation:

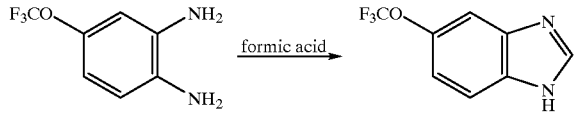

Formula (VI) provides a general definition of the phenylenediamines required as starting substances for carrying out process (d) according to the invention. In this formula (VI), $R^{12}$, $R^{15}$, $R^{16}$ and $R^{17}$ preferably, or in particular, have those meanings which have already been mentioned in connection with the description of the compounds of the formula (IVa) as being preferred, or particularly preferred, for $R^{12}$, $R^{15}$, $R^{16}$ and $R^{17}$.

The phenylenediamines of the formula (VI) are known; their preparation is described, for example, in DE-A 3 605 977, DE-A 3 621 215 or DE-A 4 237 564.

When carrying out process (b) according to the invention, suitable halogenating agents are, preferably, elemental halogen or N-halogenoimides, such as N-bromo-succinimide or N-chloro-succinimide.

Diluents which are suitable for carrying out process (b) according to the invention are all customary inert organic solvents. The following can preferably be used: aliphatic, alicyclic or aromatic hydrocarbons such as petroleum ether, hexane, heptane, cyclohexane, methylcyclohexane, benzene, toluene, xylene or decalin; furthermore halogenated hydrocarbons, such as chlorobenzene, dichlorobenzene, dichloromethane, chloroform, tetrachloromethane, dichloroethane or trichloroethane; moreover ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; furthermore nitriles, such as acetonitrile, propionitrile, n- or i-butyronitrile or benzonitrile, or else amides, such as N,N-dimethylformamide, N,N-dimethylacetamide, N-methylformamide, N-methylpyrrolidone and hexamethylphosphoric triamide.

Suitable acid-binding agents for carrying out process (b) according to the invention are all customary inorganic and organic acid acceptors. The following can preferably be used: the hydrides, hydroxides, amides, alcoholates, acetates, carbonates or hydrogen carbonates of alkaline earth metals or alkali metals, such as sodium hydride, sodium amide, sodium methylate, sodium ethylate, potassium tert-butylate, sodium hydroxide, potassium hydroxide, ammonium hydroxide, sodium acetate, potassium acetate, calcium acetate, sodium carbonate, potassium carbonate, potassium hydrogen carbonate, furthermore ammonium acetate or ammonium carbonate, or tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

When carrying out process (b) according to the invention, the reaction temperatures can be varied within a substantial range. In general, the process is carried out at temperatures between −20° C. and +120° C., preferably between 0° C. and 80° C.

When carrying out process (b) according to the invention and also when carrying out the other processes according to the invention, the reactions are generally carried out under atmospheric pressure. However, it is also possible to carry out the reactions under elevated pressure or, in the event that no gaseous components are employed, under reduced pressure.

When carrying out process (b) according to the invention, an equivalent amount, or else an excess, of halogenating agent is generally employed per mole of benzimidazole of the formula (IV). Working-up is carried out by customary methods.

If 2-bromo-5-trifluoromethoxy-1H-benzimidazole and sodium chloride are used as starting substances, the course of process (c) according to the invention can be illustrated by the following equation:

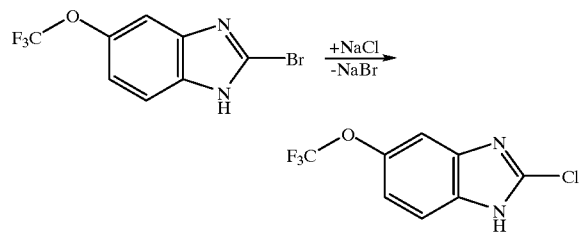

Formula (IIb) provides a general definition of the bromobenzimidazoles required for carrying out process (c) according to the invention. In this formula (IIb), $R^{12}$, $R^{13}$, $R^{14}$ and $R^{15}$ preferably, or in particular, have those meanings which have already been mentioned in connection with the description of the compounds of the formula (IIa) according to the invention as being preferred, or particularly preferred, for $R^{12}$, $R^{13}$, $R^{14}$ and $R^{15}$.

The compounds of the formula (IIb) are intermediates according to the invention and can be prepared by process (b) according to the invention.

Hydrofluoric acid, hydrochloric acid or hydriodic acid, furthermore required for carrying out process (c) according to the invention, are generally known chemicals for synthesis.

Formula (V) provides a general definition of the salts alternatively also required as reactants for carrying out process (c) according to the invention. In this formula, M preferably represents an alkali metal, in particular lithium, sodium or potassium, or a quaternary ammonium, sulphonium, sulphoxonium or phosphonium ion, preferably tetraalkylammonium, having in each case 1 to 12 carbon atoms in the individual alkyl chains, and $X^2$ represents fluorine, chlorine or iodine.

The salts of the formula (V) are known chemicals for synthesis.

Suitable diluents for carrying out process (c) according to the invention are all customary inert organic solvents. The following can preferably be used: aliphatic, alicyclic or aromatic hydrocarbons such as petroleum ether, hexane, heptane, cyclohexane, methylcyclohexane, benzene, toluene, xylene or decalin; furthermore halogenated hydrocarbons such as chlorobenzene, dichlorobenzene, dichloromethane, chloroform, tetrachloromethane, dichloroethane or trichloroethane; furthermore ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; moreover ketones, such as acetone, butanone, methyl isobutyl ketone or cyclohexanone; in addition nitrites, such as acetonitrile, propionitrile, n- or i-butyronitrile or benzonitrile; furthermore amides, such as N,N-dimethylformamide, N,N-dimethylacetamide, N-methylformanilide, N-methylpyrrolidone or hexamethylphosphoric triamide; and also esters, such as methyl acetate or ethyl acetate, and sulphoxides, such as dimethyl sulphoxide, and sulphones, such as sulpholane. If appropriate, the reaction can also be carried out in a two-phase system, for example in a mixture of toluene and water.

When carrying out process (c) according to the invention, the reaction temperatures can, again, be varied within a substantial range. In general, the process is carried out at temperatures between −20° C. and +150° C., preferably between 0° C. and 120° C.

When carrying out process (c) according to the invention, an equivalent amount, or else an excess, of the reactant in question is generally employed per mole of bromobenzimidaole. Working-up is carried out by customary methods.

Formula (III) provides a general definition of the halides furthermore required as reactants for carrying out process (a) according to the invention In this formula (III), A preferably, or in particular, has the meaning wich has already been mentioned in connection with the description of the compounds of the formula (I) according to the invention as being preferred, or particularly preferred, for A $X^1$ preferably represents chlorine or bromine.

The halides of the formula (III) are known and/or can be prepared by known processes (J. Heterocyclic Chem. 1981, 997–1006).

Suitable diluents for carrying out process (a) according to the invention are all inert organic solvents. The following can preferably be used: aliphatic, alicyclic or aromatic hydrocarbons, such as petroleum ether, hexane, heptane, cyclohexane, methylcyclohexane, benzene, toluene, xylene or decalin; halogenated hydrocarbons, such as chlorobenzene, dichlorobenzene, dichloromethane, chloroform, tetrachloromethane, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; ketones, such as acetone, butanone, methyl isobutyl ketone or cyclohexanone; nitrites, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate, sulphoxides, such as dimethyl sulphoxide, and sulphones, such as sulpholane.

If appropriate, process (a) according to the invention is carried out in the presence of a suitable acid acceptor. Suitable acid acceptors are all customary inorganic or organic bases. The following can preferably be used: the hydrides, hydroxides, amides, alcoholates, acetates, carbonates or hydrogen carbonates of alkaline earth metals or alkali metals, such as sodium hydride, sodium amide, sodium methylate, sodium ethylate, potassium tert-butylate, sodium hydroxide, potassium hydroxide, sodium acetate, potassium acetate, calcium acetate, sodium carbonate, potassium carbonate, potassium hydrogen carbonate or sodium hydrogen carbonate, furthermore ammonium hydroxide, ammonium acetate or ammonium carbonate, and also tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

When carrying out process (a) according to the invention, the reaction tenths can be varied within a substantial range. In general, the process is carried out at temperature between 0° C. and 150° C., preferably between 20° C. and 120° C.

To carry out process (a) according to the invention, 1 to 15 mol, preferably 1 to 2 mol, in particular 1 to 1.3 mol, of halide of the formula (III) are generally employed per mole of benzimidazole derivative of the formula (II).

Process (a) according to the invention is generally carried out under atmospheric pressure. However, it is also possible to carry out the process under elevated or reduced pressure, in general between 0.1 bar and 10 bar.

Working-up is carried out by customary methods.

The halogenobenzimidazoles of the formula (I) can be converted into acid addition salts or metal salt complexes.

Suitable acids for preparing acid addition salts of the compounds of the formula (I) are preferably those which have already been mentioned as preferred acids in connection with the description of the acid addition salts according to the invention.

The acid addition salts of the compounds of the formula a) can be obtained in a simple manner by customary salt formation methods, for example by dissolving a compound of the formula (I) in a suitable inert solvent and adding the acid, for example hydrochloric acid, and isolated in a known manner, for example by filtration, and, if appropriate, purified by washing with an inert organic solvent.

Suitable salts for the preparation of metal salt complexes of the compounds of the formula (I) are preferably those salts of metals which have already been mentioned as being preferred metal salts in connection with the description of the metal salt complexes according to the invention.

The metal salt complexes of the compounds of the formula (I) can be obtained in a simple manner by customary methods, for example by dissolving the metal salt in alcohol, for example ethanol, and adding the solution to compounds of the formula (I). Metal salt complexes can be isolated in a known manner, for example by filtration, and, if appropriate, purified by recrystallization.

The active compounds according to the invention have a potent microbicidal activity and can be employed in practice for controlling undesirable microorganisms. The active compounds are suitable for use as crop protection agents, in particular as fungicides in crop protection and also in the protection of materials.

Fungicidal agents are employed in crop protection for controlling Plasmodiophoromycetes, Oomycetes, Chytridiomycetes, Zygomycetes, Ascomycetes, Basidiomycetes and Deuteromycetes.

Bactericidal agents are employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above may be mentioned as examples, but not by way of limitation: Xanthomonas species, such as, for example, *Xanthomonas campestris* pv. *oryzae*; Pseudomonas species, such as, for example, *Pseudomonas syringae* pv. *lachrymans*; Erwinia species, such as, for example, *Erwinia amylovora*; Pythium species, such as, for example, *Pythium ultimum*; Phytophthora species, such as, for example, *Phytophthora infestans*; Pseudoperonospora species, such as, for example, *Pseudoperonospora humuli* or *Pseudoperonospora cubensis*; Plasmopara species, such as, for example, *Plasmopara viticola*; Bremia species, such as, for example, *Bremia lactucae*, Peronospora species, such as, for example, *Peronospora pisi* or *P. brassicae*; Erysiphe species, such as, for example, *Erysiphe graminis*; Sphaerotheca species, such as, for example, *Sphaerotheca fuliginea*; Podosphaera species, such as, for example, *Podosphaera leucotricha*; Venturia species, such as, for example, *Venturia inaequalis*; Pyrenophora species, such as, for example, *Pyrenophora teres* or *P. graminea* (conidia form: Drechslera, syn: Helminthosporium); Cochliobolus species, such as, for example, *Cochliobolus sativus* (conidia form: Drechslera, syn: Helminthosporium); Uromyces species, such as, for example, *Uromyces appendiculatus*; Puccinia species, such as, for example, *Puccinia recondita*; Sclerotinia species, such as, for example, *Sclerotinia sclerotiorum* Tilletia species, such as, for example, *Tilletia caries*; Ustilago species, such as, for example, *Ustilago nuda* or *Ustilago avenae*; Pellicularia species, such as, for example, *Pellicularia sasakii*; Pyricularia species, such as, for example, *Pyricularia oryzae*; Fusarium species, such as, for example, *Fusarium culmorum*; Botrytis species, such as, for example, *Botrytis cinerea*; Septoria species, such as, for example, *Septoria nodorum*; Leptosphaeria species, such as, for example, *Leptosphaeria nodorum*; Cercospora species, such as, for example, *Cercospora canescens*; Alternaria species, such as, for example, *Alternaria brassicae* and Pseudocercosporella species, such as, for example, *Pseudocercosporella herpotrichoides*.

The fact that the active compounds are well tolerated by plants at the concentrations required for controlling plant diseases permits the treatment of aerial parts of plants, of propagation stock and seeds, and of the soil.

The active compounds according to the invention can be employed particularly successfully for controlling diseases in fruit and vegetable growing and viticulture, such as, for example, against Phytophthora or Plasmopara species, or for controlling rice diseases, such as, for example, against the pathogen causing rice blast disease (*Pyricularia oryzae*).

In the protection of materials, the substances according to the invention can be employed for protecting industrial materials against infection with, and destruction by, undesired microorganisms.

Industrial materials in the present context are understood as meaning non-live materials which have been prepared for use in industry. For example, industrial materials which are intended to be protected by active compounds according to the invention from microbial change or destruction can be glues, sizes, paper and board, textiles, leather, wood, paints and plastic articles, cooling lubricants and other materials which can be infected with, or destroyed by, microorganisms. Parts of production plants, for example cooling-water circuits, which may be impaired by the multiplication of microorganisms may. also be mentioned within the scope of the materials to be protected. Industrial materials which may be mentioned within the scope of the present invention are preferably glues, sizes, papers and boards, leather, wood, paints, cooling lubricants and heat-transfer liquids.

Microorganisms, capable of bringing about degradation of, or change in, the industrial materials, which may be mentioned are, for example, bacteria, fungi, yeasts, algae and slime organisms. The active compounds or agents according to the invention preferably act against fungi, in particular moulds, and against slime organisms and algae.

Microorganisms of the following genera may be mentioned as examples: Alternaria, such as *Alternaria tenuis*, Aspergillus, such as *Aspergillus niger*, Chaetomium, such as *Chaetomium globosum*, Coniophora, such as *Coniophora puetana*, Lentinus, such as *Lentinus tigrinus*, Penicillium, such as *Penicillium glaucum*, Polyporus, such as *Polyporus versicolor*, Aureobasidium, such as *Aureobasidium pullulans*, Sclerophoma, such as *Sclerophoma pityophila*, Trichoderma, such as *Trichoderma viride*, Escherichia, such as *Escherichia coli*, Pseudomonas, such as *Pseudomonas aeruginosa* and Staphylococcus, such as *Staphylococcus aureus*.

Depending on their particular physical and/or chemical properties, the active compounds can be converted to the customary formulations, such as solutions, emulsions, suspensions, powders, foams, pastes, granules, aerosols and microencapsulations in polymeric substances.

These formulations are produced in a known manner, for example by mixing the active compounds with extenders, that is, liquid solvents, liquefied gases under pressure, and/or solid carriers, optionally with the use of surfactants, that is emulsifiers and/or dispersants, and/or foam formers. In the case of the use of water as an extender, organic solvents can, for example, also be used as auxiliary solvents. The following are mainly suitable as liquid solvents: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil factions, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water, liquefied gaseous extenders or carriers are to be understood as meaning liquids which are gaseous at ambient temperature and under atmospheric pressure, for example aerosol propellants such as halogenated hydrocarbons, or else butane, propane, nitrogen and carbon dioxide; suitable solid carriers are: for example ground natural minerals such as kaolins, clays, talc, chalk, quartz, attapulgite, montmorillonite or diatomaceous earth, and ground synthetic minerals such as highly disperse silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example non ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates; suitable dispersants are: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, or else natal phospholipids such as cephalins and lecithins and synthetic phospholipids can be used in the formulations. Other additives can be mineral and vegetable oils.

It is possible to use colourants such as inorganic pigments, for example iron oxide, titanium oxide and Prussian Blue, and organic dyestuff such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

The activity and the spectrum of action of the active compounds can be increased by adding, if appropriate, other antimicrobially active compounds, fungicides, bactericides, herbicides, insecticides or other active compounds for widening the spectrum of action or achieving specific effects, such as, for example, an additional protection against insects. These mixtures may have a wider spectrum of action than the compounds according to the invention.

In many cases, synergistic effects are achieved, i.e. the activity of the mixture exceeds the activity of the individual components. Examples of particularly advantageous co-components in mix are the following compounds:

Fungicides:

2-aminobutane; 2-anilino-4-methyl-6-cyclopropyl-pyrimidine; 2',6'-bromo-2-methyl-4'-trifluoromethoxy-4'-trifluoro-methyl-1,3-thiazole-5-carboxanilide; 2,6-dichloroN-(4-trifluoromethylbenzyl)benzamide; (E)-2-methoxyimino-N-methyl-2-(2-phenoxyphenyl) acetamide; 8-hydroxyquinoline sulphate; methyl (E)-2-{2-[6(2-cyanophenoxy)-pyrimidin-4-yloxy]-phenyl}-3-methoxyacrylate; methyl (E)-methoximino [alpha-(o-tolyloxy)-o-tolyl]-acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazin, carboxin, quinomethionate, chloroneb, chloropicrin, chlorothalonil, chlozolinate, cufraneb, cymoxanil, cyproconazole, cyprofuram, dichlorophen, diclobutrazol, diclofluanid, diclomezin, dicloran, diethofencarb, difenoconazole, dimethirimol, dimethomorph, diniconazole, dinocap, diphenylamine, dipyrithion, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetyl-aluminum, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, pimaricin, piperalin, polyoxin, probenazole, prochloraz, procymidone, propamocarb, propiconazole, propineb, pyrazophos, pyrifenox, pyrimethanil, pyroquilon, quintozene (PCNB), sulphur and sulphur preparations, tebuconazole, tecloftalam, tecnazene, tetraconazole, thiabendazole, thicyofen, thiophanate-methyl, thiram, tolclophos-methyl, tolylfluanid, triadimefon, triadimenol, triazoxide, trichlamide, tricyclazole, tridemorph, triflumizole, triforine, triticonazole, validamycin A, vinclozolin, zineb, ziram Bactericides:

bronopol, dichlorophen nitrapyrin, nickel dimethyldithiocarbamate, kasugamycin, octhilinone, furancarboxylic acid, oxetracyclin, probenazole, streptomycin, tecloftalam, copper sulphate and other copper preparations Insecticides/Acaricides/Nematicides:

abamectin, acephate, acrinathrin, alanycarb, aldicarb, alphamethrin, amitraz, avermectin, AZ 60541, azadirachtin, azinphos A, azinphos M, azocyclotin, Bacillus thuringiensis, 4-bromo-2-(4-chlorophenyl)-1-(ethoxymethyl)-5-(trifluoromethyl)-1H-pyrrole-3-cabonitrile, bendiocarb, benfuracarb, bensultap, betacyfluthrin, bifenthrin, BPMC, brofenprox, bromophos A, bufencarb, buprofezin, butocarboxim, butylpyridaben, cadusafos, carbaryl, carbofuran, carbophenothion, carbosulfan, cartap, chloethocarb, chlorethoxyfos, chlorfenvinphos, chlorfluazuron, chlormephos, N-[(6-chloro-3-pyridinyl)-methyl]-N'cyano-N-methyl-ethanimidamide, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton M, demeton S, demeton S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, fluazuron, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lambda-cyhalothrin, lufenuron, malathion, mecarbam, mevinphos, mesulfenphos, metaldehyde, methacrifos, methamidophos, methidathion, methiocarb, methomyl, metolcarb, milbemectin, monocrotophos, moxidectin, naled, NC 184, nitenpyram, omethoate, oxamyl, oxydemethon M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyrachlophos, pyridaphenthion, pyresmethrin, pyrethrum, pyridaben, pyrimidifen, pyriproxifen, quinalphos, salithion, sebufos, silafluofen, sulfotep, sulprofos, tebufenozid, tebufenpyrad tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, zetamethrin.

A mixture with other known active compounds, such as herbicides, or with fertilizers and growth regulators is also possible.

The active compound combinations preferably comprise 0.1 to 99.9%, in particular 1 to 75%, particularly preferably 5 to 50%, of the active compound, the remainder to 100% being made up by one or more of the abovementioned co-components.

The active compounds can be used as such or in the form of their formulations or the use forms prepared therefrom, such as ready-to-use solutions, suspensions, wettable powders, pastes, soluble powders, dusts and granules. They are used in the customary manner, for example by pouring, spraying, atomizing, spreading, dusting, foaming, brushing on and the like. It is furthermore possible to apply the active compounds by the ultra-low volume method or to inject the active compound formulation, or the active compound itself into the soil. The seed of the plants can also be treated.

In the treatment of parts of plants, the active compound concentrations in the use forms can be varied within a substantial range. They are, in general, between 1 and 0.0001% by weight, preferably between 0.5 and 0.001% by weight.

In the treatment of seed, amounts of active compound of from 0.001 to 50 g, preferably 0.01 to 10 g, are generally required per kilogram of seed.

In the treatment of the soil, active compound concentrations of from 0.00001 to 0.1% by weight, preferably from 0.0001 to 0.02% by weight, are required at the site of action.

The compositions used for the protection of industrial materials generally comprise an amount of 1 to 95%, preferably 10 to 75%, of the active compounds.

The use concentrations of the active compounds according to the invention depend on the species and the occurrence of the microorganisms to be controlled and on the composition of the material to be protected. The optimal rate of application can be determined by test series. In general, the use concentrations are in the range of from 0.001 to 5% by weight, preferably 0.05 to 1.0% by weight, based on the material to be protected.

The preparation and use of active compounds according to the invention are illustrated by the examples which follow.

PREPARATION EXAMPLES

Example 1

Process (a)

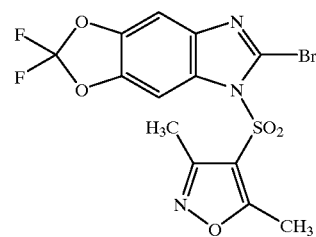

(I-1)

0.2 g (5 mmol) of sodium hydride (60%) is added at room temperature to a stirred mixture of 1.4 g (5 mmol) of 2-bromo-6,6-difluoro-[1,3]dioxolo[4,5-f]benzimidazole and 30 ml of absolute tetrahydrofuran, and the reaction mixture is then stirred for 30 minutes at room temperature. 1.0 g (5.5 mmol) of 3,5-dimethylisoxazole-4-sulphonyl chloride is then added, and the mixture is stirred for a further 3 hours at room temperature. For working-up, the reaction mixture is poured into 100 ml of water. The resulting mixture is extracted twice using in each case 50 ml of ethyl acetate. The combined organic phases are dried over sodium sulphate and concentrated under reduced pressure. The residue which remains is chromatographed on silica gel using methylene chloride as the eluent. This gives 1.2 g (75% of theory) of 1-(3,5-dimethylisoxazole-4-sulphonyl)-2-bromo-6,6-difluoro-[1,3]-dioxolo-[4,5-f]benzimidazole in the form of a colourless solid of melting point 130–134° C.

Preparation of Precursors

Process (b)

(II-1)

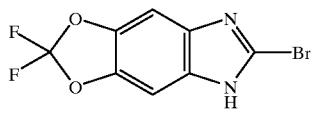

2.0 g (10 mmol) of 6,6-difluoro[1,3]dioxolo[4,5-f]benzimidazole are added to a suspension of 0.48 g (12 mmol) of 60% sodium hydride in 20 ml of absolute dimethylformamide, the mixture is stirred for 30 minutes at 20° C., 2.2 g (12 mmol) of N-bromosuccinimide are then added, and the mixture is stirred for a further 30 minutes at the same temperatures mixture is poured onto 250 g of ice, brought to pH=4 using glacial acetic acid and extracted three times using in each case 100 ml of ethyl acetate. The combined organic extracts are dried over sodium sulphate and concentrated in vacuo. The residue which remains is stirred with 50 ml of water, and the resulting residue is filtered off and dried.

This gives 2.3 g (83% of theory) of 2-bromo-6,6-difluoro[1,3]dioxolo[4,5-f]benzimidazole as a white solid of a melting range of 160 to 164° C.

Process (d)

(IV-1)

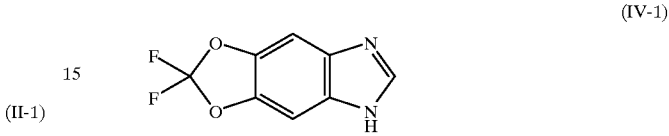

80 ml of 98% strength formic acid are added to 37.6 g (0.2 mol) of 5,6-diamino-2,2-difluorobenzodioxole, and the mixture is refluxed for 4 hours. After cooling, the mixture is rendered alkaline using 2N sodium hydroxide solution. The precipitate is filtered off, washed using 200 ml of water and dried.

This gives 38.1 g (95% of theory) of 6,6-difluoro[1,3]dioxolo[4,5-f]benzimidazole in the form of a solid.

The substances listed in the table which follows are also prepared by the methods given above.

TABLE 17

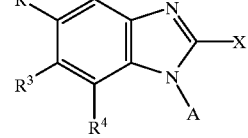

| Ex. No. | $R^1$ | $R^2$ | $R^3$ | $R^4$ | A | X | Physical constant |
|---|---|---|---|---|---|---|---|
| 2 | H | —O—CF$_3$—CF$_2$—O— | | H | 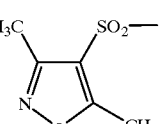 | Br | m.p.: 90° C. (Decomp.) |
| 3 | H | —O—CF$_2$—CF$_2$—O— | | H | 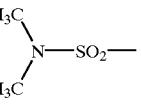 | Br | m.p.: 115–119° C. |
| 4 | H | —O—CF$_2$—O— | | H | 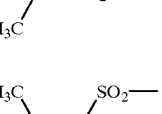 | Br | m.p.: 112–115° C. |
| 5 | H | H | 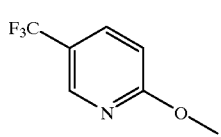 | H | 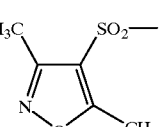 | Cl | m.p.: 48–53° C. |

TABLE 17-continued
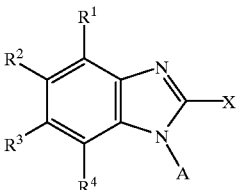
| Ex. No. | R¹ | R² R³ | R⁴ | A | X | Physical constant |
|---|---|---|---|---|---|---|
| 6 | H | —O—CF$_2$—O— | H | 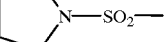 | Br | m.p.: 117–124° C. |
| 7 | H | —O—CF$_2$—O— | H | 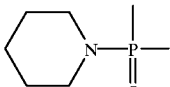 | Br | $^1$H NMR*) (DMSO): 1.37–1.56 (m, 6H); 2.97–3.40 (m, 4H); 7.75(s, $^1$H); 7.98 (s, 1H) |
| 8 | H | —O—CF$_2$—O— | H | 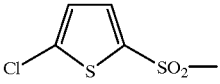 | Br | m.p.: 181–185° C. |
| 9 | H | —O—CF$_2$—O— | H | 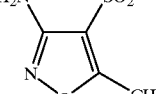 | Br | m.p.: 180–183° C. |
| 10 | H | —O—CF$_2$—O— | H | 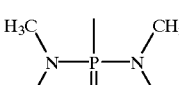 | Br | m.p.: 85–90° C. |
| 11 | H | —O—CF$_2$—O— | H | 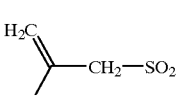 | Br | m.p.: 133–136° C. |
| 12 | H | —O—CF$_2$—O— | H | 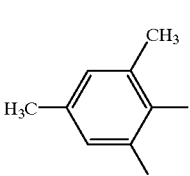 | Br | m.p.: 132–136 |
| 13 | H | —O—CF$_2$—O— | H | 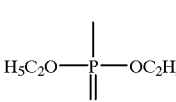 | Br | m.p.: 53–58° C. |
| 14 | H | —O—CF$_2$—O— | H | 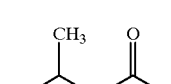 | Br | m.p.: 94–97° C. |
| 15 | H | —O—CF$_2$—O— | H | H$_3$C—SO$_2$— | Br | m.p.: 170–173° C. |
| 16 | H | —O—CF$_2$—O— | H | H$_5$C$_2$—SO$_2$— | Br | m.p.: 97–101° C. |

TABLE 17-continued
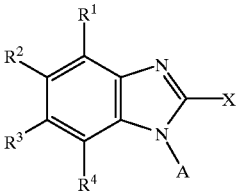
| Ex. No. | R¹ | R² | R³ | R⁴ | A | X | Physical constant |
|---|---|---|---|---|---|---|---|
| 17 | H | —O—CF₃—CF₃—O— | | H | 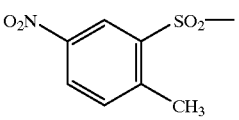 | Br | m.p.: 170–174° C. |
| 18 | H | —O—CF₃—CF₃—O— | | H | 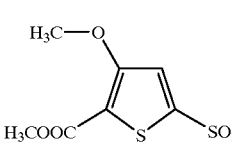 | Br | m.p.: 153–156° C. |
| 19 | H | —O—CH₃ | H | H | 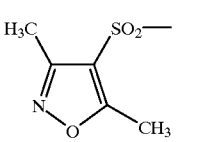 | Cl | m.p.: 105–108° C. |
| 20 | H | —O—CF₃—O— | | H | 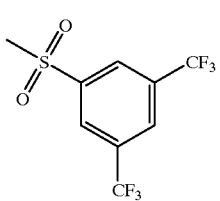 | Br | m.p.: 162–164° C. |
| 21 | H | —OCH₃ | H | H | 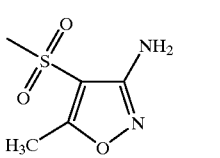 | —Cl | m.p.: 127–130° C. |
| 22 | H | H | 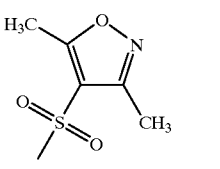 | H | 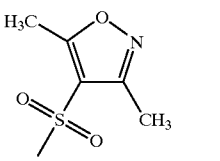 | —Cl | m.p.: 80–84° C. |
| 23 | H | H | H | H |  | —Cl | m.p.: 181–183° C. |

TABLE 17-continued
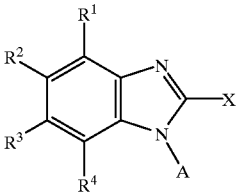
| Ex. No. | R¹ | R² | R³ | R⁴ | A | X | Physical constant |
|---|---|---|---|---|---|---|---|
| 24 | H | H | 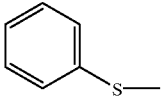 | H | 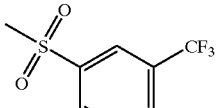 | —Cl | m.p.: 97–104° C. |
| 25 | H | H | 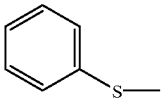 | H | 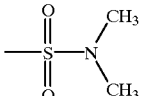 | —Cl | NMR: 2.82 |
| 26 | H | —O—CF$_2$—O— | | H | 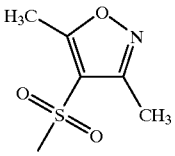 | —Cl | m.p.: 129–131° C. |
| 27 | H | —Cl | —Cl | H | 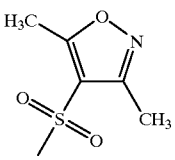 | —Br | m.p.: 185–190° C. |
| 28 | H | —O—CF$_2$—CF$_2$—O— | | H | 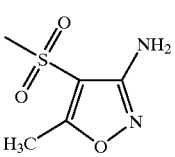 | —Br | m.p.: 180–184° C. |
| 29 | H | —O—CF$_2$—CF$_2$—O— | | H | —SO$_2$—CH$_3$ | —Br | m.p.: 170–174° C. |
| 30 | H | —O—CF$_2$—O— | | H | 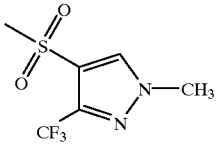 | —Br | m.p.: 170–174° C. |
| 31 | H | H | H | H | 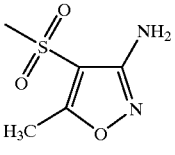 | —Cl | m.p.: 200° C. |

TABLE 17-continued

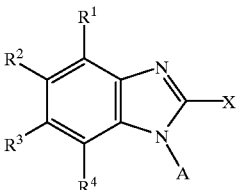

| Ex. No. | R¹ | R² | R³ | R⁴ | A | X | Physical constant |
|---|---|---|---|---|---|---|---|
| 32 | H | H | 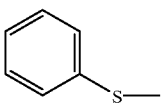 | H |  | —Cl | m.p.:130–136° C. |
| 33 | H | —O—CF₂—CF₂—O— | | H | 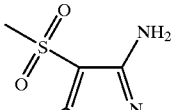 | —Cl | m.p.: 130–136° C. |
| 34 | H | —O—CF₂—O— | | H | 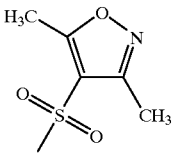 | —Br | m.p.: 219–223° C. |
| 35 | H | H | 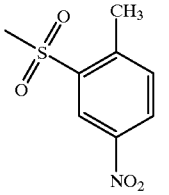 | H | 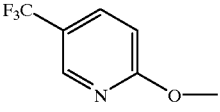 | Cl | m.p.: 170–173° C. |

*) The ¹H NMR spectra were recorded in hexa-deuterodimethyl sulphoxide (DMSO-D₆) using tetramethylsilane (TMS) as the internal standard. The value given is the chemical shift, δ, in ppm.

Example 36

Process (c)

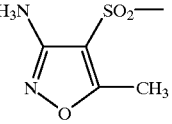 (II-2)

Hydrogen chloride gas is passed for 2 hours at 120° C. into a solution of 2.8 g (10 mmol) of 2-bromo-6,6-difluoro [1,3]dioxolo[4,5-f]benzimidazole in 30 ml of dimethylformamide. The mixture is poured onto 200 g of ice/water and extracted three times using in each case 80 ml of ethyl acetate. The combined organic extracts are dried over sodium sulphate and concentrated under reduced pressure. The residue is chromatographed on silica gel using diethyl ether. This gives 0.5 g (21.5% of theory) of 2-chloro-6,6-difluoro[1,3]dioxolo[4,5-f]benzimidazole as a white solid of melting point>220° C.

Example 37

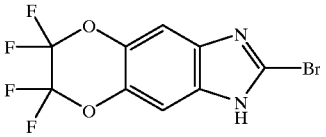 (II-3)

2-Bromo-6,6,7,7-tetrafluoro[1,4]dioxino[2,3-f] benzimidazole is also prepared by the method described in Example 1.

Melting point: 170–174° C.

Example 38

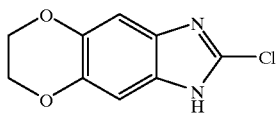
(II-4)

2-Chloro[1,4]dioxino[2,4-f]benzimidazole is also prepared by the method described in Example 1.

Melting point: 150° C.

Example 39

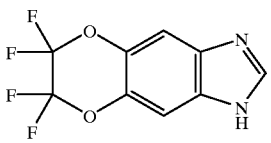
(IV-2)

6,6,7,7-Tetrafluoro[1,4]dioxino[2,3-f]benzimidazole is also prepared by the method described in Example 1.

Melting point: 70–74° C.

USE EXAMPLES

Example A

Phytophthora Test (Tomato)/Protective

Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew moist. After the spray coating has dried on, the plants are inoculated with an aqueous spore suspension of *Phytophthora infestans*.

The plants remain in an incubation cabin at 100% relative atmospheric humidity and approx. 20° C.

The test is evaluated 3 days after inoculation. 0% means an efficacy which corresponds to the control while an efficacy of 100% means that no disease is observed.

Active compounds, active compound concentrations and test results can be seen from the table which follows.

TABLE A

Phytophthora test (tomato)/protective

| Active compound | Efficacy in % based on the untreated control at an active compound concentration of 50 ppm |
|---|---|
| According to the invention: | |
| (1) | 99 |
| (2) | 97 |
| (3) | 86 |
| (15) | 94 |
| (16) | 94 |

TABLE A-continued
Phytophthora test (tomato)/protective)
| Active compound | Efficacy in % based on the untreated control at an active compound concentration of 50 ppm |
|---|---|
| (17) 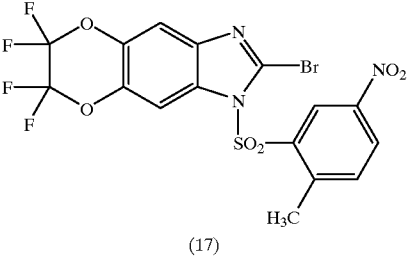 | 97 |
| (19) 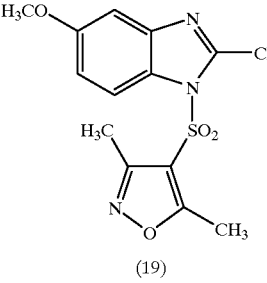 | 96 |
| (9) 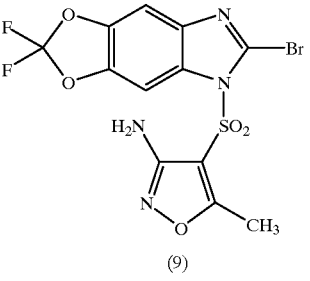 | 95 |
| (23) 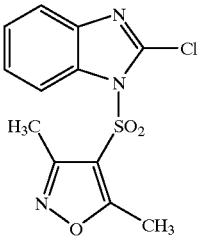 | 99 |
| (26) 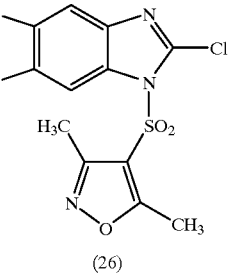 | 99 |
| (22) 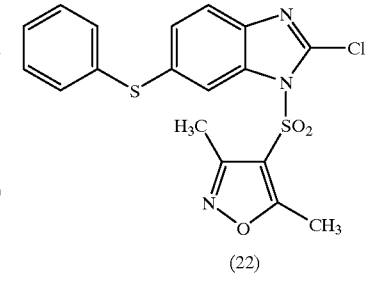 | 99 |
| (28) 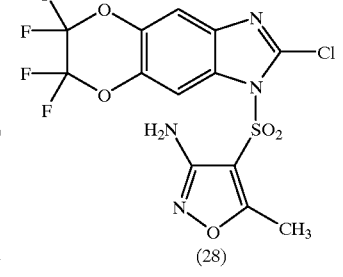 | 97 |
| (29) 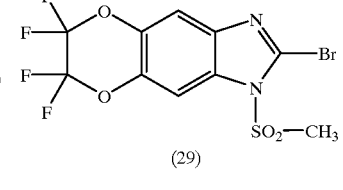 | 97 |
| (27) 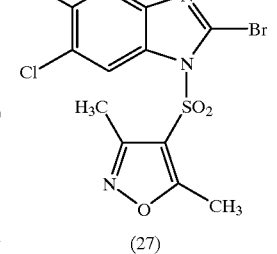 | 95 |

Example B

Plasmopara Test (Vines)/Protective
Solvent: 4.7 parts by weight of acetone
Emulsifier: 0.3 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are inoculated with an aqueous spore suspension of *Plasmopara viticola* and then remain in a humid chamber at 20 to 22° C. and 100% relative atmospheric humidity for 1 day. The plants are then placed in a greenhouse at 21° C. and about 90% atmospheric humidity for 5 days. The plants are then moistened and placed in a humid chamber for 1 day.

The test is evaluated 6 days after inoculation. 0% means an efficacy which corresponds to the control while an efficacy of 100% means that no disease is observed.

Active compounds, active compound concentrations and test results can be seen from the table which follows.

TABLE B

Plasmopora test (vines)/protective

| Active compounds | Efficacy in % based on the untreated control at an active compound concentration of 50 ppm |
|---|---|
| According to the invention: | |
| 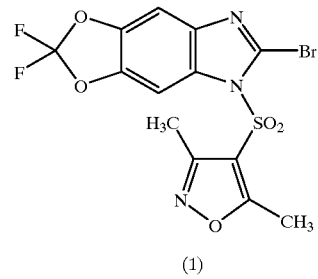 (1) | 99 |
| 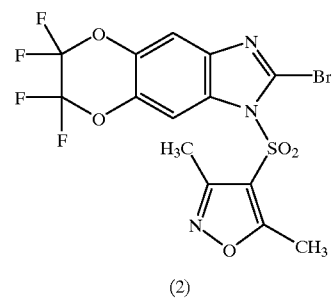 (2) | 93 |
| 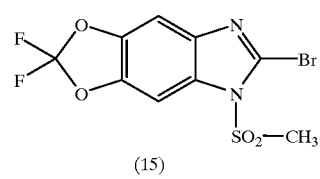 (15) | 92 |
| 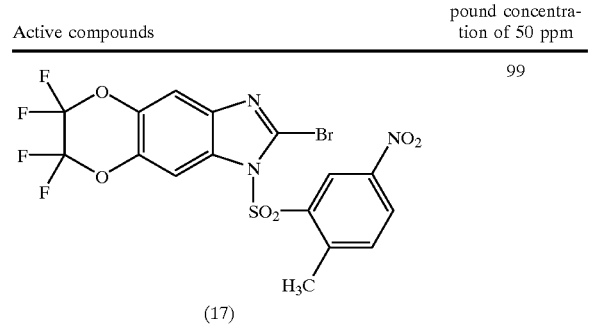 (17) | 99 |
| 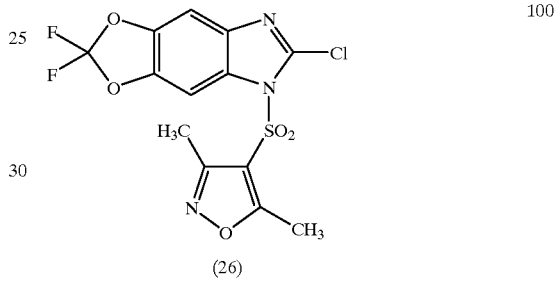 (26) | 100 |
| 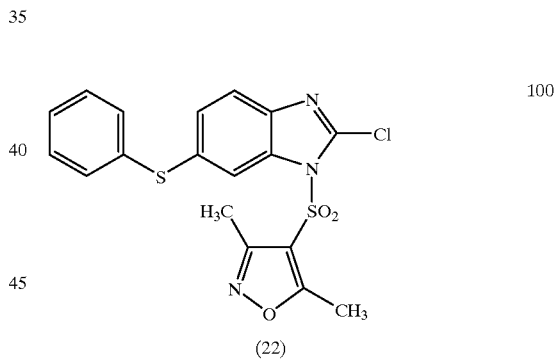 (22) | 100 |
| 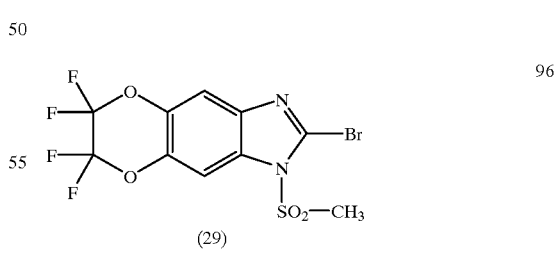 (29) | 96 |

Example C

Venturia Test (Apple)/Protective
Solvent: 4.7 parts by weight of acetone
Emulsifier: 0.3 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are inoculated with an aqueous conidia suspension of the pathogen causing apple scab (*Venturia inaequalis*) and then remain in an incubation cabin at 20° C. and 100% relative atmospheric humidity for 1 day.

The plants are then placed in a greenhouse at 20° C. and a relative atmospheric humidity of about 70%.

The test is evaluated 12 days after inoculation. 0% means an efficacy which corresponds to the control while an efficacy of 100% means that no disease is observed.

Active compounds, active compound concentrations and test results can be seen from the table which follows.

TABLE C

Venturia test (apple)/protective

| Active compound | Efficacy in % based on the untreated control at an active compound concentration of 100 ppm |
|---|---|
| According to the invention: | |
| 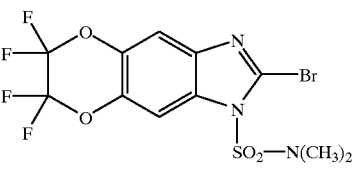 (3) | 89 |

What is claimed is:
1. A halogenobenzimidazole of the formula

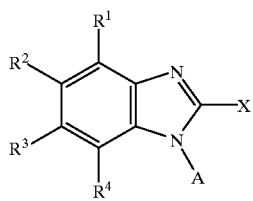

(I)

in which
R$^1$, R$^2$, R$^3$ and R$^4$ independently of one another represent hydrogen, fluorine, chlorine, bromine, iodine, cyano, nitro, straight-chain or branched alkyl having 1 to 8 carbon atoms, straight-chain or branched halogenoalkyl having 1 to 6 carbon atoms and 1 to 13 identical or different halogen atoms, straight-chain or branched alkoxy having 1 to 8 carbon atoms, straight-chain or branched halogenoalkoxy having 1 to 6 carbon atoms and 1 to 13 identical or different halogen atoms, straight-chain or branched alkylthio having 1 to 8 carbon atoms, straight-chain or branched halogenoalkylthio having 1 to 6 carbon atoms and 1 to 13 identical or different halogen atoms, straight-chain or branched alkylsulphinyl having 1 to 8 carbon atoms, straight-chain or branched halogenoalkylsulphinyl having 1 to 6 carbon atoms and 1 to 13 identical or different halogen atoms, straight-chain or branched alkylsulphonyl having 1 to 8 carbon atoms, straight-chain or branched halogenoalkylsulphonyl having 1 to 6 carbon atoms and 1 to 13 identical or different halogen atoms, cycloalkyl having 3 to 6 carbon atoms which is optionally monosubstituted to pentasubstituted by identical or different substituents selected from the group consisting of halogen and alkyl having 1 to 4 carbon atoms, or represent hydroxycarbonyl, alkylcarbonyl having 1 to 6 carbon atoms in the straight-chain or branched alkyl moiety, alkoxycarbonyl having 1 to 6 carbon atoms in the straight-chain or branched alkoxy moiety, cycloalkylcarbonyl having 3 to 6 carbon atoms in the cycloalkyl moiety, cycloalkoxycarbonyl having 3 to 6 carbon atoms in the cycloalkyl moiety, or represent —Z—R$^5$, wherein
R$^5$ represents aryl having 6 to 10 carbon atoms, it being possible for each of these radicals to be monosubstituted to trisubstituted by identical or different substituents selected from the group consisting of halogen, cyano, nitro, alkyl having 1 to 4 carbon atoms, alkoxy having 1 to 4 carbon atoms, alkylthio having 1 to 4 carbon atoms, halogenoalkyl having 1 to 4 carbon atoms and 1 to 5 identical or different halogen atoms, halogenoalkoxy having 1 to 4 carbon atoms and 1 to 5 identical or different halogen atoms, halogenoalkylthio having 1 to 4 carbon atoms and 1 to 5 identical or different halogen atoms, alkylsulphinyl having 1 to 4 carbon atoms, alkylsulphonyl having 1 to 4 carbon atoms, halogenoalkylsulphinyl having 1 to 4 carbon atoms and 1 to 5 identical or different halogen atoms and halogenoalkylsulphonyl having 1 to 4 carbon atoms and 1 to 5 identical or different halogen atoms, or
Z represents a direct bond, and —CH$_2$—, O, S, SO, SO$_2$, or CO, or represents —CO—O—, the oxygen atom being bonded to R$^5$, or represents —SO$_2$—O—, the sulphur atom being bonded to R$^5$, or represents —S—CH$_2$—SO$_2$—, the sulphur atom of the thio group being bonded to R$^5$, or
R$^1$ and R$^2$, or R$^2$ and R$^3$, or R$^3$ and R$^4$ in each case together also represent an alkylene chain having 3 or 4 members in which one or two (non-adjacent) carbon atoms can be replaced by oxygen atoms and which is optionally monosubstituted to hexasubstituted by halogen, alkyl having 1 to 4 carbon atoms or halogenoalkyl having 1 to 4 carbon atoms and 1 to 9 halogen atoms, X represents fluorine, chlorine, bromine or iodine,
and
A represents the group —SO$_2$—R$^8$, wherein
R$^8$ represents thienyl, it being possible for this radical to be monosubstituted to trisubstituted by identical or different substituents selected from the group consisting of fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl, ethylsulphonyl, trifluoromethyl, difluoromethoxy, trifluoromethoxy, difluoromethylthio, trifluoromethylthio, trifluoromethylsulphinyl, trifluoromethylsulphonyl, methylamino, ethylamino, n- or i-propylamino, dimethylamino, diethylamino, acetyl, propinonyl, acetyloxy, methoxycarbonyl, ethoxycarbonyl, methylsulphonyloxy, ethylsulphonyloxy, hydroxyiminomethyl, hydroxyiminoethyl, methoxyiminomethyl, ethoxyiminomethyl, methoxyiminoethyl and ethoxyiminoethyl,
or an addition product thereof with an acid or a metal salt.

2. A microbicidal composition comprising a microbicidally effective amount of a halogenobenzimidazole according to claim 1 or an acid addition salt or metal salt complex thereof and an inert diluent.

3. A method for the control of undesired microorganisms comprising applying an effective amount therefor of a halogenobenzimidazole according to claim 1 or an acid addition salt or metal salt complex thereof to the microorganisms or to their habitat or to an area from which it is desired to exclude such microorganisms.

4. A compound of the formula

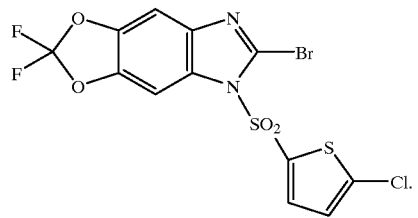

* * * * *

UNITED STATES PATENT AND TRADEMARK OFFICE
CERTIFICATE OF CORRECTION

PATENT NO.    : 6,387,939 B1
DATED         : May 14, 2002
INVENTOR(S)   : Lutz Assmann et al.

It is certified that error appears in the above-identified patent and that said Letters Patent is hereby corrected as shown below:

<u>Title page, Item [54] and Column 1, line 1,</u>
Change "HALOGENZIMIDAZOLES" to -- HALOBENZIMIDAZOLES --

Signed and Sealed this

Ninth Day of September, 2003

JAMES E. ROGAN
*Director of the United States Patent and Trademark Office*